(12) United States Patent
Mor (10) Patent No.: US 7,985,538 B2
(45) Date of Patent: Jul. 26, 2011

(54) DRUG RESISTANCE AND METHODS OF REVERSING

(75) Inventor: Gil G. Mor, Cheshire, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 12/224,244

(22) PCT Filed: Feb. 23, 2007

(86) PCT No.: PCT/US2007/004707
§ 371 (c)(1),
(2), (4) Date: Feb. 25, 2009

(87) PCT Pub. No.: WO2007/100650
PCT Pub. Date: Sep. 7, 2007

(65) Prior Publication Data
US 2009/0220427 A1    Sep. 3, 2009

Related U.S. Application Data (60) Provisional application No. 60/776,304, filed on Feb. 23, 2006, provisional application No. 60/788,168, filed on Mar. 31, 2006.

(51) Int. Cl.
*C12Q 1/00* (2006.01)
*G01N 33/53* (2006.01)
(52) U.S. Cl. .................... 435/4; 6/7.1; 6/7.23
(58) Field of Classification Search ............ None
See application file for complete search history.

(56) References Cited

FOREIGN PATENT DOCUMENTS
WO    WO 2005/054814 A1    6/2005
WO    WO 2007/042554 A2    4/2007

OTHER PUBLICATIONS

Entrez Gene report (National library of medicine) 2010.*
Wang et al Br. J. Haematol, 118:638-45, 2002.*
Kavallaris et al JCI. 100:1282-93, 1997.*
Abrahams et al J of Immun. 173:4286-96, 2004.*
MyD88 search result, 2010.*
Bonnert et al, FEBS Lett. 402:81-84, 1997.*
Abrahams et al., Toll-like receptors and their role in the trophoblast. Placenta. Aug. 2005;26(7):540-7. Review.
Abrahams et al., Divergent trophoblast responses to bacterial products mediated by TLRs. J Immunol. Oct. 1, 2004;173(7):4286-96.
Abrahams et al., Epithelial ovarian cancer cells secrete functional Fas ligand. Cancer Res. Sep. 1, 2003;63(17):5573-81.
Ackerman et al., Topotecan in cervical cancer. Int J Gynecol Cancer. 2007;17(6):1215-23.
Akira et al., Toll-like receptor signalling. Nat Rev Immunol. Jul. 2004;4(7):499-511. Review.
Akira, Toll-like receptor signaling. J Biol Chem. Oct. 3, 2003;278(40):38105-8. Epub Jul. 30, 2003. Review.
Alvero et al., Molecular phenotyping of human ovarian cancer stem cells unravels the mechanisms for repair and chemoresistance. Cell Cycle. Jan. 1, 2009;8(1):158-66.
Alvero et al., Molecular mechanism of phenoxodiol-induced apoptosis in ovarian carcinoma cells. Cancer. Feb. 1, 2006;106(3):599-608.
Alvero et al., Telomerase prolongs the lifespan of normal human ovarian surface epithelial cells without inducing neoplastic phenotype. J Soc Gynecol Investig. Dec. 2004;11(8):553-61.
Anderson et al., Establishment of dorsal-ventral polarity in the Drosophila embryo: the induction of polarity by the Toll gene product. Cell. Oct. 1985;42(3):791-8.
Asselin et al., XIAP regulates Akt activity and caspase-3-dependent cleavage during cisplatin-induced apoptosis in human ovarian epithelial cancer cells. Cancer Res. Mar. 1, 2001;61(5):1862-8.
Balkwill et al., Cancer: an inflammatory link. Nature. Sep. 23, 2004;431(7007):405-6.
Beachy et al., Mending and malignancy. Nature. Sep. 23, 2003;431(7007):402.
Behrens et al., Characterization of a cis-diamminedichloroplatinum(II)-resistant human ovarian cancer cell line and its use in evaluation of platinum analogues. Cancer Res. Jan. 15, 1987;47(2):414-8.
Bellmunt et al., Clinical activity of vinflunine in transitional cell carcinoma of the urothelium and other solid tumors. Semin Oncol. Jun. 2008;35(3 Suppl 3):S34-43.
Byrd-Leifer et al., The role of MyD88 and TLR4 in the LPS-mimetic activity of Taxol. Eur J Immunol. Aug. 2001;31(8):2448-57.
Coussens et al., Inflammation and cancer. Nature. Dec. 19-26, 2002;420(6917):860-7. Review.
Dan et al., Akt phosphorylation and stabilization of X-linked inhibitor of apoptosis protein (XIAP). J Biol Chem. Feb. 13, 2004;279(7):5405-12. Epub Nov. 25, 2003.
Dan et al., Phosphatidylinositol-3-OH kinase/AKT and survivin pathways as critical targets for geranylgeranyltransferase I inhibitor-induced apoptosis. Oncogene. Jan. 22, 2004;23(3):706-15.
DeVisser et al., The interplay between innate and adaptive immunity regulates cancer development. Cancer Immunol Immunother. Nov. 2005;54(11):1143-52. Epub May 12, 2005. Review.
Ding et al., Characterization of a method for profiling gene expression in cells recovered from intact human prostate tissue using RNA linear amplification. Prostate Cancer Prostatic Dis. 2006;9(4):379-91. Epub Jun. 20, 2006.
Ding et al., Shared actions of endotoxin and taxol on TNF receptors and TNF release. Science. Apr. 20, 1990;248(4953):370-2.

(Continued)

*Primary Examiner* — Misook Yu
*Assistant Examiner* — Lei Yao
(74) *Attorney, Agent, or Firm* — Wolf, Greenfield & Sacks, P.C.

(57) ABSTRACT

Described herein is a cellular marker, MyD88, useful for assessing an individual's (patient's) sensitivity (or resistance) to chemotherapy, particularly sensitivity (or resistance) to chemotherapeutic drugs, such as plant alkaloids (e.g., a taxane, such as paclitaxel or docetaxel). As described herein, Applicants provide a method by which it is possible to determine whether an individual (cancer cells in an individual) is sensitive to chemotherapy with plant alkaloids (e.g., a taxane, such as paclitaxel or docetaxel). Early identification of chemoresistance in patients with cancer is of utmost importance, particularly since it makes it possible to provide the most appropriate therapy.

13 Claims, 2 Drawing Sheets

OTHER PUBLICATIONS

Flick et al., Apoptosis-based evaluation of chemosensitivity in ovarian cancer patients. J Soc Gynecol Investig. May 2004;11(4):252-9.

Giudice et al., Endometriosis. Lancet. Nov. 13-19, 2004;364(9447):1789-99. Review.

Goto et al., Activation of Toll-like receptors 2, 3, and 4 on human melanoma cells induces inflammatory factors. Mol Cancer Ther. Nov. 2008;7(11):3642-53.

Gutierrez et al., The Fas/Fas-ligand system: a mechanism for immune evasion in human breast carcinomas. Breast Cancer Res Treat. Apr. 1999;54(3):245-53.

Harmey et al., Lipopolysaccharide-induced metastatic growth is associated with increased angiogenesis, vascular permeability and tumor cell invasion. Int J Cancer. Oct. 10, 2002;101(5):415-22.

Heigener et al., Multicenter randomized open-label phase III study comparing efficacy, safety, and tolerability of conventional carboplatin plus etoposide versus dose-intensified carboplatin plus etoposide plus lenograstim in small-cell lung cancer in "extensive disease" stage. Am J Clin Oncol. Feb. 2009;32(1):61-4.

Holcik et al., XIAP: apoptotic brake and promising therapeutic target. Apoptosis. Aug. 2001;6(4):253-61. Review.

Kamsteeg et al., Phenoxodiol—an isoflavone analog—induces apoptosis in chemoresistant ovarian cancer cells. Oncogene. May 1, 2003;22(17):2611-20.

Kaplan et al., Nonparametric estimation from incomplete observations. J Am Stat Assn. 1958;55:457-81.

Kelly et al., TLR-4 signaling promotes tumor growth and paclitaxel chemoresistance in ovarian cancer. Cancer Res. Apr. 1, 2006;66(7):3859-68.

Matsuzaki et al., Differential expression of genes in eutopic and ectopic endometrium from patients with ovarian endometriosis. Fertil Steril. Sep. 2006;86(3):548-53. Epub Jul. 3, 2006.

McMillan et al., Systemic inflammatory response predicts survival following curative resection of colorectal cancer. Br J Surg. Feb. 2003;90(2):215-9.

Medzhitov et al., Decoding the patterns of self and nonself by the innate immune system. Science. Apr. 12, 2002;296(5566):298-300.

Medzhitov, Toll-like receptors and innate immunity. Nat Rev Immunol. Nov. 2001;1(2):135-45. Review.

Medzhitov et al., Innate immunity: the virtues of a nonclonal system of recognition. Cell. Oct. 31, 1997;91(3):295-8. Review.

Metzner et al., Evidence of the involvement of phosphatidylinositol 3-kinase in the migration, actin stress fiber formation, and alpha v beta 3-integrin-mediated adherence of human melanoma cells. J Invest Dermatol. Oct. 1996;107(4):597-602.

Nakanishi et al., Nuclear factor-kappaB inhibitors as sensitizers to anticancer drugs. Nat Rev Cancer. Apr. 2005;5(4):297-309. Review.

Norgauer et al., Expression and growth-promoting function of the IL-8 receptor beta in human melanoma cells. J Immunol. Feb. 1, 1996;156(3):1132-37.

O'Dwyer et al., Antitumor activity and biochemical effects of aphidicolin glycinate (NSC 303812) alone and in combination with cisplatin in vivo. Cancer Res. Feb. 1, 1994;54(3):724-9.

Pidgeon et al., The role of endotoxin/lipopolysaccharide in surgically induced tumour growth in a murine model of metastatic disease. Br J Cancer. Dec. 1999;81(8):1311-7.

Richmond et al., Growth factor and cytogenetic abnormalities in cultured nevi and malignant melanomas. J Invest Dermatol. Mar. 1986;86(3):295-302.

Richmond et al., Purification of melanoma growth stimulatory activity. J Cell Physiol. Dec. 1986;129(3):375-84.

Riman et al., Review of epidemiological evidence for reproductive and hormonal factors in relation to the risk of epithelial ovarian malignancies. Acta Obstet Gynecol Scand. Sep. 2004;83(9):783-95. Review.

Robinson et al., Soluble mediators of inflammation during tumor development. Adv Cancer Res. 2005;93:159-87. Review.

Sapi et al., Resistance of ovarian carcinoma cells to docetaxel is XIAP dependent and reversible by phenoxodiol. Oncol Res. 2004;14(11-12):567-78.

Schmitz et al., Regulation of death receptor-mediated apoptosis pathways. Int J Biochem Cell Biol Nov.-Dec. 2000;32(11-12):1123-36. Review.

Schwartz, Current diagnosis and treatment modalities for ovarian cancer. Cancer Treat Res. 2002;107:99-118. Review.

Szczepanski et al., Triggering of Toll-like receptor 4 expressed on human head and neck squamous cell carcinoma promotes tumor development and protects the tumor from immune attack. Cancer Res. Apr. 1, 2009;69(7):3105-13. Epub Mar. 24, 2009.

Sekizawa et al., Malignant transformation of endometriosis: application of laser microdissection for analysis of genetic alterations according to pathological changes. Med Electron Microsc. Jun. 2004;37(2):97-100. Review.

Takeuchi et al., Toll-like receptors; their physiological role and signal transduction system. Int Immunopharmacol. Apr. 2001;1(4):625-35. Review.

Vicari et al., Chemokines in cancer. Cytokine Growth Factor Rev. Apr. 2002;13(2):143-54. Review.

Wang et al., MyD88 is involved in the signalling pathway for Taxol-induced apoptosis and TNF-alpha expression in human myelomonocytic cells. Br J Haematol. Aug. 2002;118(2):638-45.

Yuan et al., AKT2 inhibition of cisplatin-induced JNK/p38 and Bax activation by phosphorylation of ASK1: implication of AKT2 in chemoresistance. J Biol Chem. Jun. 27, 2003;278(26):23432-40. Epub Apr. 15, 2003.

* cited by examiner

Figure 1

DRUG RESISTANCE AND METHODS OF REVERSING

CROSS REFERENCE TO RELATED APPLICATIONS

This application is a national stage filing under 35 U.S.C. §371 of international application PCT/US2007/004707, filed Feb. 23, 2007, which was published under PCT Article 21(2) in English, and claims the benefit under 35 U.S.C. §119(e) of U.S. Provisional Application Ser. No. 60/776,304, filed Feb. 23, 2006 and U.S. Provisional Application Ser. No. 60/788,168, filed Mar. 31, 2006. The entire teachings of each referenced application are incorporated herein by reference.

BACKGROUND OF THE INVENTION

A woman has a 1 in 67 chance of developing ovarian cancer, which is the leading cause of gynecologic cancer deaths. The American Cancer Society estimated that, in 2006, there would be about 20,180 new cases of the disease in the United States and that about 15,310 women would die from the disease that year. Often, ovarian cancer is not diagnosed until it has progressed and the prognosis is not good. The standard first-line chemotherapy for patients with ovarian cancer is a platinum-taxane combination regimen. More than eighty percent of patients will respond initially to this treatment. However, fewer than 10% will remain in remission. Schwartz P E, *Cancer Treat Res*, 2002; 107:79-118. Improved methods of detecting and treating ovarian cancer are needed.

SUMMARY OF INVENTION

Described herein is a cellular marker, MyD88, useful for assessing an individual's (patient's) sensitivity (or resistance) to chemotherapy, particularly sensitivity (or resistance) to chemotherapeutic drugs, such as plant alkaloids (e.g., a taxane, such as paclitaxel or docetaxel). As described herein, Applicants provide a method by which it is possible to determine whether an individual (cancer cells in an individual) is sensitive to chemotherapy with plant alkaloids (e.g., a taxane, such as paclitaxel or docetaxel). Early identification of chemoresistance in patients with cancer is of utmost importance, particularly since it makes it possible to provide the most appropriate therapy.

Evidence suggests that an inflammatory profile of cytokines and chemokines persisting at a particular site would lead to the development of a chronic disease. Recent studies implicate bacterial infection as one possible link between inflammation and carcinogenesis, but the crucial molecular pathways involved remain unknown. Applicants hypothesized that one upstream signaling pathway that might lead to inflammation in carcinogenesis is mediated by Toll-like receptors (TLRs). Described herein is an adaptive mechanism acquired by ovarian cancer cells that allows them to promote a pro-inflammatory environment and develop chemo-resistance. TLR-4-MyD88 signaling pathway is a risk factor for developing cancer and represents a novel target for the development of bio-modulators.

Provided herein is new evidence that links TLR-4 signaling, inflammation and chemoresistance in ovarian cancer cells. In particular, Applicants demonstrate a link between TLR-4-MyD88 signaling, inflammation, tumor growth and chemo-resistance. Described herein is the expression of TLR-4 in cancer cells, as exemplified by epithelial ovarian cancer (EOC) cells and the differential effect of TLR-4 ligation by LPS and paclitaxel in MyD88 positive (MyD88$^+$) and MyD88 negative (MyD88$^-$) EOC cells. About 85% to 90% of ovarian cancers are epithelial ovarian carcinomas. The work described herein, such as the link between TLR-4-MyD88 signaling, inflammation, tumor growth and chemoresistance, provides the basis for assessing responsiveness (sensitivity or resistance) to chemotherapeutic drugs, such as a woman's responsiveness (sensitivity or resistance) to chemotherapeutic drugs, particularly paclitaxel, as well as for treating or reducing the development of a cancer characterized by elevated expression of MyD88.

Applicants demonstrate that in EOC cells, signaling through TLR-4 and MyD88 represent a major source of pro-inflammatory cytokines, which promote tumor growth. Furthermore, they have identified a new mechanism for the acquisition of paclitaxel chemo-resistance and therefore, a novel target for the development of molecularly directed therapy in paclitaxel resistant ovarian cancer. In the presence of paclitaxel, EOC cells that express MyD88 show an increase in cell proliferation, secretion and production of proinflammatory cytokines and activation of anti-apoptotic proteins. Cells that do not express MyD88 are paclitaxel sensitive, do not shown NF-κB activation and do not produce inflammatory cytokines.

In one embodiment, this invention relates to a method of assessing the sensitivity or resistance of cancer cells to chemotherapy, particularly chemotherapy with a plant alkaloid, such as a taxane (e.g., paclitaxel or docetaxel), comprising assaying MyD88 expression in the cancer cells. MyD88 expression can be assessed by, for example, detecting the presence or absence and/or quantity of MyD88 itself. Alternatively, nucleic acid encoding MyD88 (e.g., mRNA, DNA) can be assessed MyD88 expression (a positive result of the analysis) indicates that the individual (patient) from whom the sample was obtained is resistant to such chemotherapy (e.g., chemotherapy with a plant alkaloid, such as a taxane, such as paclitaxel or docetaxel). Conversely, if the sample is negative for MyD88 expression, the individual (patient) is sensitive to such chemotherapy. For example, if cancer cells (e.g., ovarian cancer cells) obtained from an individual are MyD88 negative (MyD88$^-$), they are sensitive to chemotherapy with a plant alkaloid (e.g., a taxane, such as paclitaxel or docetaxel). Here, the individual's prognosis is good (better than if the patient is resistant to the chemotherapeutic). MyD88 positive cancer cells (e.g., ovarian cancer cells) are resistant to chemotherapy with a plant alkaloid (e.g., a taxane, such as paclitaxel or docetaxel). Alternatively, the level of MyD88 in cancer cells (e.g. in ovarian cancer cells) can be determined and compared with a reference or standard (e.g., a correlation between level of MyD88 in cancer cells of the same type as the cells being assessed and the extent/degree of sensitivity/resistance to a chemotherapeutic, such as a correlation between the level of MyD88 in ovarian cancer cells and sensitivity/resistance to paclitaxel). For example, the relationship between MyD88 level in a type of cancer cell (e.g., ovarian cancer cells) and resistance to a plant alkaloid, such as a taxane (e.g., paclitaxel or docetaxel) can be determined empirically using known methods and a reference or standard established. Resistance/sensitivity to such a chemotherapeutic can be correlated with a range of MyD88 levels and a scale produced. MyD88 level determined in a sample obtained from an individual (e.g., MyD88 level in ovarian cancer cells) can be compared with the correlation or scale and an indication of resistance or sensitivity determined. Alternatively, a "cutoff" MyD88 value (e.g., a MyD88 level below which cancer cells are more sensitive than resistant to a plant alkaloid, such as a taxane (e.g., paclitaxel or docetaxel)) can be established and levels determined for cells obtained from a patient compared with that value, to assess their resistance or sensitivity to the plant alkaloid. If the level of MyD88 is greater than the cutoff value, the cancer cells are resistant to such chemotherapy. If the level of MyD88 is less than the cutoff value, the cells are sensitive to such chemotherapy. The method can be carried out to assess the sensitivity or resistance of an individual suffering from, for example, ovarian cancer, breast cancer, head and/or neck cancer, prostate cancer, non-small cell lung cancer, small cell lung cancer, bladder cancer, stomach cancer, or Kaposi's sarcoma.

In a specific embodiment, the invention relates to a method of assessing the sensitivity or resistance of cancer cells to a taxane, such as paclitaxel or docetaxel, used to treat cancer, such as ovarian cancer, breast cancer, head and/or neck cancer, prostate cancer, non-small cell lung cancer, small cell lung cancer, bladder cancer, stomach cancer, or Kaposi's sarcoma. In this embodiment, the method of assessing the sensitivity or resistance of cancer cells to chemotherapy, particularly chemotherapy with a taxane (e.g., paclitaxel or docetaxel), comprises assaying MyD88 expression in the cancer cells. MyD88 expression can be assessed by, for example, detecting the presence or absence and/or quantity of MyD88 itself. Alternatively, nucleic acid encoding MyD88 (e.g., mRNA, DNA) can be assessed. MyD88 expression (a positive result of the analysis) indicates that the individual (patient) from whom the sample was obtained is resistant to such chemotherapy (e.g., chemotherapy with a taxane, such as paclitaxel or docetaxel). Conversely, if the sample is negative for MyD88 expression, the individual (patient) is sensitive to such chemotherapy. Alternatively, the level of MyD88 in cancer cells (e.g. in ovarian cancer cells) can be determined and compared with a reference or standard (e.g., a correlation between level of MyD88 in cancer cells of the same type as the cells being assessed and the extent/degree of sensitivity/ resistance to a chemotherapeutic, such as a correlation between the level of MyD88 in ovarian cancer cells and sensitivity/resistance to paclitaxel). For example, the relationship between MyD88 level in a type of cancer cell (e.g., ovarian cancer cells) and resistance to a taxane (e.g., paclitaxel or docetaxel) can be determined empirically using known methods and a reference or standard established. Resistance/sensitivity to a taxane (e.g., paclitaxel or docetaxel) can be correlated with a range of MyD88 levels and a scale produced. MyD88 level determined in a sample obtained from an individual (e.g., MyD88 level in ovarian cancer cells) can be compared with the correlation or scale and an indication of resistance or sensitivity determined. Alternatively, the reference expression level can be, for example, the level of MyD88 in noncancer cells; such as ovarian cells that are not cancer cells or other cells (e.g., cells from a source other than ovarian tissue), which may or may not be cancer cells. These cells, referred to as reference cells, can be obtained from the individual whose paclitaxel sensitivity/resistance is being assessed or from another individual or individuals. The reference expression levels can be determined at the time an individual is assessed for paclitaxel sensitivity/resistance or can be pre-established reference expression levels (reference expression standard). Alternatively, a "cutoff" MyD88 value (e.g., a MyD88 level below which cancer cells are more sensitive than resistant to a taxane (e.g., paclitaxel or docetaxel)) can be established and levels determined for cells obtained from a patient compared with that value, to assess their resistance or sensitivity to the plant alkaloid. If the level of MyD88 is greater than the cutoff value, the cancer cells are resistant to such chemotherapy. If the level of MyD88 is less than the cutoff value, the cells are sensitive to such chemotherapy. The method can be carried out to assess the sensitivity or resistance of ovarian cancer cells (e.g., epithelial ovarian cancer cells), breast cancer cells, head and/or neck cancer cells, prostate cancer cells, non-small cell lung cancer cells, small cell lung cancer cells, bladder cancer cells, stomach cancer cells, or Kaposi's sarcoma cells.

In one embodiment, the invention relates to a method of determining MyD88 (e.g., level of expression, presence or absence of expression) in cells isolated from a tumor, such as by using laser microdissection and dot-blot analysis. In a particular embodiment, laser microdissection is used to obtain a tumor sample that contains a sufficient number of cancer cells to permit assessment of MyD88 (e.g. from about 500 to about 5,000 cells). The sample can be obtained, for example, from a biopsy or a tumor after surgery. Frozen sections can be used, for example. The cells are lysed, using known methods and the product is analyzed (e.g., by Western blot) for MyD88 expression. MyD88 expression can be assessed by, for example, detecting the presence or absence and/or quantity of MyD88 itself. Alternatively, nucleic acid encoding MyD88 (e.g., mRNA, DNA) can be assessed. MyD88 expression (a positive result of the analysis) indicates that the patient from whom the sample was obtained is resistant to paclitaxel. Conversely, if the sample is negative for MyD88 expression, the patient is sensitive to paclitaxel and the patient's prognosis is good (e.g., better than if the patient is resistant to paclitaxel). Samples used for the analysis can be obtained by other methods known to those of skill in the art and can be analyzed for MyD88 expression by other art recognized methods as well.

Also described herein is a method of inhibiting proliferation of a cancer cell, comprising contacting the cell (such as an ovarian cancer cell, particularly human ovarian cancer cells) with a compound that inhibits, directly or indirectly, signaling through the TLR4:MyD88 pathway. In addition, this invention relates to a method of reducing production of proinflammatory cytokines, which promote tumor growth, by cancer cells and, as a result, reducing the extent to which tumor growth occurs. Such methods can be carried out to inhibit proliferation of cancer cells of many types in which there is an active TLR4:MyD88 signaling pathway, including, but not limited to, ovarian cancer cells (e.g., epithelial ovarian cancer cells), breast cancer cells, head and/or neck cancer cells, prostate cancer cells, non-small cell lung cancer cells, small cell lung cancer cells, bladder cancer cells, stomach cancer cells, and Kaposi's sarcoma cells.

This invention is also a method of reducing (partially or totally) tumor growth, comprising contacting tumor cells in which there is an active TLR4:MyD88 signaling pathway with a compound that inhibits, directly or indirectly, signaling through the TLR4:MyD88 signaling pathway. Also the subject of this invention is a method of treating or preventing cancer, such as a cancer characterized by an active TLR4: MyD88 signaling pathway, in an individual in need thereof, comprising administering to the individual (e.g., a human suffering from or at risk of developing such a cancer) an effective amount of a compound that inhibits, directly or indirectly, signaling through the TLR4:MyD88 pathway. In a specific embodiment, the invention is a method of treating or preventing ovarian cancer, in an individual (such as a woman suffering from or at risk of developing ovarian cancer characterized by an active TLR4:MyD88 signaling pathway), comprising administering to the individual (e.g., the woman) an effective amount of a compound that inhibits, directly or indirectly, signaling through the TLR4:MyD89 pathway.

Also described herein is a method for inhibiting proliferation of a cancer cell, comprising contacting the cell (such as an ovarian cancer cell, particularly human ovarian cancer cells) with a compound that inhibits signaling through the TLR4:MyD88 pathway. The compound can be, for example, a TLR4 antagonist, such as a compound that inhibits activity or expression of TLR4. The TLR4 antagonist can be, for example, an antibody against TLR4, a mutated form of TLR4, a mimic of TLR4, a small molecule compound that inhibits activity and/or expression of TLR4; an antisense nucleic acid, or an siRNA. Signaling through the TLR4:MyD88 pathway can be measured, for example, by assessing the activation status of NFκB or by assessing the level of one or more pro-inflammatory cytokine (e.g., GRO-α, MCP-1, IL-6). Alternatively, the compound can be a MyD88 antagonist, such as a compound that inhibits activity or expression of MyD88. An MyD88 antagonist can be, for example, an antibody against MyD88, a mutated form of MyD88, a mimic of MyD88, a small molecule compound that inhibits activity and/or expression of MyD88, an antisense nucleic acid, or an siRNA.

Also described herein is a method of treating or preventing cancer, such as cancer characterized by elevated expression of MyD88 (e.g., ovarian cancer), in an individual (e.g., a human, such as a woman at risk for or suffering from a cancer characterized by elevated MyD88 expression, such as ovarian cancer), comprising administering to the individual (e.g., a human, such as a woman with ovarian cancer) an effective amount of a compound that inhibits signaling through the TLR4:MyD88 pathway. In the method, the compound used can be, for example, a TLR4 antagonist, such as a compound that inhibits activity or expression of TLR4. The TLR4 antagonist can be, for example, an antibody against TLR4, a mutated form of TLR4, a mimic of TLR4 a small molecule compound that inhibits activity and/or expression of TLR4, an antisense nucleic acid, or an antisense nucleic acid, or a SiRNA. Alternatively, the compound can be a MyD88 antagonist, such as a compound that inhibits activity or expression of MyD88. An MyD88 antagonist can be, for example, an antibody against MyD88, a mutated form of MyD88, a mimic of MyD88, a small molecule compound that inhibits activity and/or expression of MyD88, an antisense nucleic acid, or an siRNA.

A further embodiment of the present invention is a therapeutic compound which inhibits and, preferably, specifically inhibits, signaling through the TLR4:MyD88 pathway, such as a TLR4 antagonist (e.g., a compound that inhibits activity or expression of TLR4). The TLR4 antagonist, which can be an isolated or substantially pure form, can be an antibody against TLR4, a mutated form of TLR4, a mimic of TLR4, a small molecule compound that inhibits activity and/or expression of TLR4, an antisense nucleic acid, or an siRNA. Alternatively, the therapeutic compound can be a MyD88 antagonist (e.g., a compound that inhibits activity or expression of MyD88). The MyD88 antagonist can be, for example, an antibody against MyD88, a mutated form of MyD88, a small molecule compound that inhibits activity and/or expression of TLR4, an antisense nucleic acid, or an siRNA. A therapeutic compound can be used to treat a cancer characterized by elevated MyD88 expression, such as ovarian cancer.

A further embodiment of the invention is a method for monitoring drug treatment of an individual who has cancer (e.g., a human, such as a woman with ovarian cancer), comprising: administering a drug to the individual and assaying tissues or cells, such as cancer cells, for MyD88, wherein the expression level of MyD88 is an indicator of the disease status of the individual. For example, a decrease in expression level of MyD88 is typically an indication that the drug treatment is effective.

In another embodiment, the invention relates to a method of enhancing chemo-sensitivity in an individual who has cancer (e.g., a human, such as a woman who has ovarian cancer), in which a therapeutically effective amount of a compound which inhibits signaling through the TLR4:MyD88 pathway is administered to an individual in need thereof (such as a woman who has ovarian cancer).

This invention also relates to a method of diagnosing or aiding in diagnosing cancer in an individual (e.g., a human, such as a woman to be diagnosed for ovarian cancer), comprising assaying the expression of MyD88 in a tissue from the individual, wherein the presence of MyD88 or an expression level of MyD88 that is greater than a reference expression level is indicative of tumor tissue or precancerous tissue in the individual. The reference level can be, for example, the level of MyD88 in cells known not to be cancerous, such as cells of the same type (from the same type of organ or tissue) as that being assessed. For example, the level of MyD88 in noncancerous ovarian cells, obtained from a woman being assessed or from a different woman or women, can be the reference level.

A further embodiment of this invention relates to a method for screening for genetic susceptibility to cancer in an individual, comprising assaying the expression level of MyD88 in a tissue from the individual, wherein an expression level (an expression level known to be indicative of genetic susceptibility to cancer) of MyD88 that is greater than a reference expression level is indicative of genetic susceptibility to cancer in the individual. In a specific embodiment, the individual being assessed is a human, such as a woman being assessed for genetic susceptibility (likelihood of developing) cancer, such as a genetic susceptibility for developing ovarian cancer.

BRIEF DESCRIPTION OF THE DRAWINGS

The following figures (FIGS. 1 and 2) are Kaplan-Meier curves that illustrate the duration of progression-free interval and overall survival for patients with MyD88+ and MyD88− primary tumors. The pathological diagnosis was papillary serous adenocarcinoma of the ovary for all patients. However, the clinical course and the response to combination chemotherapy with carboplatin and paclitaxel were markedly different and correlated with MyD88 expression in the analyzed tumors.

DETAILED DESCRIPTION OF THE INVENTION

As described herein, MyD88 is a cellular marker that can be used to assess the likelihood that an individual will be responsive (will be sensitive or resistant) to chemotherapy with a plant alkaloid, such as a taxane (e.g., paclitaxel or docetaxel) and whose expression in cancer cells accurately predicts a poor response to such chemotherapy. In a specific embodiment, MyD88 is used as a cellular marker to assess the likelihood that ovarian cancer cells will respond (be sensitive or resistant) to treatment with a taxane, such as paclitaxel or docetaxel and to predict a woman's prognosis, in terms of progression-free interval and overall survival. Cancer cells in which MyD88 is expressed are resistant to taxane chemotherapy, such as treatment with paclitaxel or docetaxel; the prognosis for an individual whose cancer cells express MyD88 (are MyD88⁻) is poor (relative to the prognosis of an individual whose cancer cells do not express MyD88 (are MyD88⁺), as assessed, for example, by progression-free interval and overall survival). As also described herein, Applicants have shown that an adaptive mechanism present in cancer cells allows the cells to exhibit chemoresistance (resistance to a chemotherapeutic drug), particularly resistance to paclitaxel and more particularly resistance of ovarian cancer cells to paclitaxel. They have also shown that, in MyD88 positive cancer cells, such as in ovarian cancer cells, paclitaxel stimulates cell growth and production of proinflammatory cytokines. The work described herein, such as the link between TLR-4-MyD88 signaling, inflammation, tumor growth and chemoresistance, provides the basis for assessing an individual's responsiveness (sensitivity or resistance) to chemotherapeutic drugs, particularly paclitaxel, as well as for treating or reducing the development of a cancer characterized by elevated expression of MyD88. It provides the basis for assessing the responsiveness of cancer cells, such as ovarian cancer cells (e.g., epithelial ovarian cancer cells), breast cancer cells, head and/or neck cancer cells, prostate cancer cells, non-small cell lung cancer cells, small cell lung cancer cells, bladder cancer cells, stomach cancer cells, and Kaposi's sarcoma cells to a taxane (paclitaxel, docetaxel). It is reasonable to conclude that the TLR4:MyD88 signaling pathway in cells is a risk factor for developing cancer and a target for reducing (partially or completely) chemoresistance to a taxane, such as resistance to paclitaxel or docetaxel.

In one embodiment, the cellular marker MyD88 is used to assess the sensitivity/resistance of individuals treated with paclitaxel, a first line chemotherapy agent often used in treating ovarian cancer in women. Applicants have shown that, using the approached described herein, it is possible to determine quickly whether a patient is sensitive to paclitaxel or other taxens. Applicants have demonstrated that proteins involved in the apoptotic cascade and chemoresistance of cancer cells can be accurately detected. They have exemplified their work using epithelial ovarian cancer cells or EOC (human EOC) isolated from ovarian malignant tumors that were obtained at the time of surgery. The method can be used with a variety of cancer cell types, such as, but not limited to, breast cancer cells, head and/or neck cancer cells, prostate cancer cells, non-small cell lung cancer cells, small cell lung cancer cells, bladder cancer cells, stomach cancer cells, and Kaposi's sarcoma cells.

In one embodiment, tumor specimens are obtained and, optionally, snap-frozen in liquid nitrogen and specimens of appropriate size to provide a sufficient number of cells for analysis (e.g., 8 μm thick specimens, in the case of ovarian cancer) are stained to facilitate the selection of tumor cells. Target cells are identified based on their immunostaining and collected, such as with the laser capture microdissection (LCM) system described herein. Using CD45 staining proved to be highly useful for the identification and selection of cancer cells from tumor tissue and classification of tumors as either MyD88 positive or negative. The resulting collected cells are lysed and analyzed for MyD88, such as by Western blot or Luminex multiplex assay. In the case of EOC cells, the microdissected cells were evaluated for the expression of MyD88, FasL and XIAP by Western blot analysis.

This protocol provides a fast and easy method for analyzing protein expression in tissues, as exemplified by analysis in EOC cells, after LCM. This method was used to evaluate the correlation between MyD88 expression and clinical outcome in women with ovarian cancer. Applicants found that all patients who had MyD88 positive tumors presented with poor progression-free interval and overall survival after chemotherapy with carboplatin and paclitaxel, while the patients with MyD88 negative tumors had an excellent response to chemotherapy. This provides a molecular approach to identify taxane and, specifically, paclitaxel, chemoresistance. Toxicity from agents without therapeutic benefit can be avoided by identifying those patients who will not respond to a specific agent, such as paclitaxel. Molecular markers make it possible to design individualized treatments and improve overall survival. As described herein, Applicants have shown that the status of MyD88 expression is valuable information to have before beginning chemotherapy with paclitaxel, since that status has an impact on chemo-responsiveness.

The present invention relates to a method of assessing responsiveness of a cancer cell to a plant alkaloid, comprising determining whether the cancer cell expresses MyD88 (MyD88⁺) or does not express MyD88 (MyD88⁻), wherein if the cancer cell is MyD88⁺, it is resistant to the plant alkaloid and if the cancer cell is MyD88⁻, it is sensitive to the plant alkaloid. In one embodiment, the plant alkaloid is a taxane, such as paclitaxel or docetaxel. This method is useful to assess the responsiveness of a wide variety of cancer cells (e.g. human cancer cells) such as an ovarian cancer cell (such as an EOC cell), a breast cancer cell, a head cancer cell, a neck cancer cell, a prostate cancer cell, a non-small cell lung cancer cell, a small cell lung cancer cell, a bladder cancer cell, a stomach cancer cell, or a Kaposi's sarcoma cell.

The invention is also a method of assessing sensitivity or resistance of a cancer cell to chemotherapy with a plant alkaloid, comprising assaying expression of MyD88 in the cancer cell, wherein the cancer cell is sensitive to chemotherapy with the plant alkaloid if the cancer cell does not express MyD88 and the cancer cell is resistant to chemotherapy with the plant alkaloid if the cancer cell expresses MyD88. In one embodiment, the plant alkaloid is a taxane, such as paclitaxel or docetaxel. This method is useful with a wide variety of cancer cells (e.g., human cells), such as an ovarian cancer cell (such as an EOC cell), a breast cancer cell, a head cancer cell, a neck cancer cell, a prostate cancer cell, a non-small cell lung cancer cell, a small cell lung cancer cell, a bladder cancer cell, a stomach cancer cell, or a Kaposi's sarcoma cell.

Determining whether a cancer cell expresses MyD88 or does not express MyD88 can be carried out by detecting the presence or absence of MyD88 in the cancer cell, detecting the quantity of MyD88 in the cancer cell or detecting nucleic acid that encodes MyD88 in the cancer cell.

A further embodiment of the invention is a method of inhibiting proliferation of a cancer cell, comprising contacting the cancer cell with a compound which inhibits signaling through the TLR4:MyD88 pathway. In one embodiment, the compound is a TLR4 antagonist, such as a compound that inhibits activity or expression of TLR4. The TLR4 antagonist can be an antibody against TLR4, a mutated form of TLR4, a mimic of TLR4, a small molecule compound, an antisense nucleic acid, or an siRNA. In a further embodiment, the compound is a MyD88 antagonist, such as a compound that inhibits activity or expression of MyD88. The MyD88 antagonist can be an antibody against MyD88, a mutated form of MyD88, a mimic of MyD88, a small molecule compound, an antisense nucleic acid, and an siRNA. The method can further comprise assessing signaling through the TLR4:

MyD88 pathway after the cancer cell is contacted with the compound, wherein signaling through the TLR4:MyD88 pathway is measured by activation status of NF-κB or by determining the presence or absence of a pro-inflammatory cytokine or the level of a pro-inflammatory cytokine, such as GRO-α, MCP-1 or IL-6. This method is useful with a variety of cancer (e.g. human) cell types, such as an ovarian cancer cell (such as an EOC cell), a breast cancer cell, a head cancer cell, a neck cancer cell, a prostate cancer cell, a non-small cell lung cancer cell, a small cell lung cancer cell, a bladder cancer cell, a stomach cancer cell, or a Kaposi's sarcoma cell.

A further embodiment is a method of treating or preventing cancer in an individual, comprising administering to the individual an effective amount of a compound that inhibits signaling through the TLR4:MyD88 pathway. The compound can be a TLR4 antagonist, such as a compound that inhibits activity or expression of TLR-4. The TLR4 antagonist can be an antibody against TLR4, a mutated form of TLR4, a mimic of TLR4, a small molecule compound, an antisense nucleic acid, or an siRNA. The compound can be a MyD88 antagonist, such as a compound that inhibits activity or expression of MyD88. The MyD88 antagonist can be selected from an antibody against MyD88, a mutated form of MyD88, a mimic of MyD88, a small molecule compound, an antisense nucleic acid, and an siRNA.

The method can further comprise assessing signaling through the TLR4:MyD88 pathway after the effective amount of a compound that inhibits signaling through the TLR4:MyD88 pathway is administered to the individual, wherein signaling through the TLR4:MyD88 pathway is measured by activation status of NF-κB or by determining the presence or absence of a pro-inflammatory cytokine or the level of a pro-inflammatory cytokine, such as GRO-α, MCP-1 or IL-6. In this embodiment, the cancer can be ovarian cancer (epithelial ovarian cancer), breast cancer, head and/or neck cancer, prostate cancer, non-small cell lung cancer, small cell lung cancer, bladder cancer, stomach cancer, or Kaposi's sarcoma. The cancer typically will be human cancer, but can be cancer in non humans. In specific embodiments, the cancer is characterized by cancer cells that do not express MyD88 (MyD88⁻ cells).

An isolated therapeutic compound which specifically inhibits signaling through the TLR4:MyD88 pathway is also the subject of this invention. It can be a TLR4 antagonist, such as a compound that inhibits activity or expression of TLR4 (e.g., an antibody against TLR4, a mutated form of TLR4, a mimic of TLR4, a small molecule compound an antisense nucleic acid, and an siRNA). The therapeutic compound can be a MyD88 antagonist, such as a compound that inhibits activity or expression of MyD88 (e.g., an antibody against MyD88, a mutated form or a mimic of MyD88, a small molecule compound, an antisense nucleic acid, or an siRNA.

A method for monitoring drug treatment of an individual who has cancer is also the subject of this invention, the method comprising: administering a drug to the individual; and assaying the expression level of MyD88, wherein the expression level of MyD88 is an indicator of the disease status of the individual. The cancer can be, for example, ovarian cancer, such as human ovarian cancer (e.g., ovarian cancer in which cancer cells do not express MyD88 (MyD88⁻). Alternatively the cancer can be breast cancer, head and/or neck cancer, prostate cancer, non-small cell lung cancer, small cell lung cancer, bladder cancer, stomach cancer, or Kaposi's sarcoma. Also a subject of this invention is a method of enhancing chemo-sensitivity in an individual who has cancer, comprising administering to an individual in need thereof a therapeutically effective amount of a compound which inhibits signaling through the TLR4:MyD88 pathway. The individual might have ovarian cancer, breast cancer, head and/or neck cancer, prostate cancer, non-small cell lung cancer, small cell lung cancer, bladder cancer, stomach cancer, or Kaposi's sarcoma.

A further subject of the invention is a method of diagnosing or aiding in diagnosing cancer in an individual, comprising assaying the expression level of MyD88 in a tissue from the individual, wherein an expression level of MyD88 which is greater than a reference expression level is indicative of tumor tissue or precancerous tissue in the individual. Also the subject of this invention is a method for screening for genetic susceptibility to cancer (e.g., ovarian cancer) in an individual, comprising assaying the expression level of MyD88 in a tissue from the individual, wherein an expression level of MyD88 which is greater than a reference expression level is indicative of genetic susceptibility to cancer in the individual.

The present invention is illustrated by the following examples, which are not intended to be limiting in any way.

Materials and Methods

The following materials and methods were used in the work described in Examples 1-10.

Reagents

LPS isolated from *E. Coli* (0111:B4), carboplatin and paclitaxel were purchased from Sigma Chemical Co. (St. Louis, Mo.). The rabbit polyclonal antibody to TLR-4, clone H-80 was purchased from Santa Cruz Biotechnology Inc, (Santa Cruz, Calif.).

Patients & Samples

Tissue and ascites samples were collected from stage III/IV ovarian cancer patients. Tissues were cut in small aliquots and snap frozen in liquid nitrogen. All patients signed consent forms and the use of patient samples was approved under Yale University's Human Investigations Committee (HIC #10425).

Cell Lines

Human EOC cell lines, A2780 and CP70 (gifts from Dr. T C Hamilton (16) were propagated in RPMI plus 10% fetal bovine serum (Gemini Bio-Products, Woodland, Calif.) at 37° C. in a 5% $CO_2$ atmosphere. Primary EOC cells were isolated from malignant ovarian ascites and cultured as previously described (17). EOC cells were isolated from tumors as previously described (17, 18). The normal ovarian surface epithelial cell line immortalized with telomerase was cultured as previously described (19). Purity of the EOC cells was 100% as determined by immuno-staining for cytokeratin antigen.

Immunohistochemistry

Twenty four samples of ovarian cancer tissues were evaluated for immunocytochemistry. The expression and cellular localization of TLR-4 and MyD88 by EOC cells was performed as previously described (20). In short, sections of tumor samples (5 μm) were blocked with either 10% horse or goat serum in PBS for 1 hour at room temperature. Following three washes with PBS, samples were incubated overnight at 4° C. with either the anti-TLR-4 (Santa Cruz) or the anti-MyD88 antibody. Mouse IgG1 or rabbit serum served as negative controls. After three washes with PBS, specific staining was detected by incubating with either a peroxidase-conjugated horse anti-mouse antibody (1:1000 dilution) or a peroxidase-conjugated goat anti-rabbit antibody (1:1000 dilution) for 1 hour followed by a five-minute incubation with DAB substrate (Vector Laboratories). Cells and tissue sections were then counterstained with haematoxylin (Sigma Chemical Co.) before dehydration with ethanol and Histosolve (Shandon Inc., Pittsburgh, Pa.). Slides were then mounted with Permount (Fisher Scientific, Pittsburgh, Pa.) and visualized by light microscopy.

Cell Viability Assay

Cell viability was evaluated using a cell proliferation assay, i.e., the CELLTITER96® Aqueous One Solution Cell Proliferation Assay (Promega, Madison, Wis.) according to the manufacturer's instructions. The values from the treated cells were compared with the values generated from the untreated cells and reported as percent viability. Each experiment was performed at least three times.

Protein Preparation

Protein was extracted as previously described (17). Briefly, cell pellets were lysed in a cold solution of 1% NP40 and 0.1% SDS in PBS, with freshly added Protease Inhibitor Cocktail (20 µl/ml; Sigma Chemical Co.) and 2 mM PMSF (Sigma Chemical Co.). Protein concentration was determined by BioRad Protein Assay (BioRad, Hercules, Calif.) and proteins were stored at −40° C. until further use.

For separation of the cytoplasmic and nuclear fractions, cell pellets were processed using the NE-PER Nuclear and Cytoplasmic Extraction Kit (Pierce Biotechnology, Rockford, Ill.) according to the manufacturer's instructions.

SDS-PAGE and Western Blots

Twenty µg protein were denatured in sample buffer (2.5% SDS, 10% glycerol, 5% β-mercapto-ethanol, 0.15 M Tris (pH=6.8) and 0.01% bromophenol blue) and subjected to 12% SDS-PAGE as previously described (17). Antibodies used: rabbit anti-TLR-4 (Santa Cruz Biotechnology, Santa Cruz, Calif., 1:1,000), rabbit anti-MyD88 (eBiosciences, San Diego, Calif., 1:1,000), mouse anti-NF-κB (Santa Cruz Biotechnology, 1:1,000), mouse anti-DNA topoisomerase 1 (BD Biosciences, San Jose, Calif., 1:500) and, rabbit anti-actin (Sigma Chemical Co., 1:10,000). Proteins were visualized using enhanced chemiluminescence (Pierce Biotechnology).

RNA Isolation and RT-PCR

Total RNA was isolated using the RNeasy Mini Kit (Qiagen, Valencia, Calif.) according to the manufacturer's instructions. Reverse transcription was performed on 5 µg of total RNA using the First Strand cDNA Synthesis kit (Amersham Biosciences, Buckinghamshire, U.K.) according to the manufacturer's instructions. The primers used for amplification of human TLR-4 are as follows: (Forward primer) TGGATACGTTTCCTTATAAG (SEQ ID NO:1); (Reverse primer) GAAATGGAGGCACCCCTTC (SEQ ID NO:2). 30 cycles of PCR were performed at 95° C. for 15 seconds, 54° C. for 45 seconds and 72° C. for 60 seconds. The size of the product was 449 bp.

Caspase Assay

Ten µg of protein in a 50 µl total volume was mixed with 50 µl of equilibrated reagents of a caspase assay kit, i.e., the CASPASE GLO™ 3/7 Assay (Promega). After incubating at room temperature for 1 h, luminescence was measured using TD 20/20 Luminometer (Turner Designs, Sunnyvale, Calif.). Blank values were subtracted and fold-increase in activity was calculated based on activity measured from untreated cells. Each sample was measured in triplicate.

Cytokine and Chemokine Studies

Chemokine production was determined using the Human Cytokine Array kit, III (for cell culture supernatants) (RayBiotech, Atlanta, Ga.) as previously described (20). The intensity of the signals was quantified by densitometry using a digital imaging analysis system and 1D Image Analysis Software (Eastman Kodak Company). The signal intensities were normalized against the positive controls on each array membrane, which were given the arbitrary unit of 1. Any expression levels below 0.2 units were considered non-significant.

The concentrations of the IL-6, GRO-α, MCP-1 were evaluated by ELISA, according to the manufacturer's instructions. (R&D Systems, Minneapolis, Minn.)

A panel of 10 cytokines, pro and anti-inflammatory, was simultaneously evaluated using the Fast Quant Human II kit (Whatman/Schleicher & Schuell) according to the manufacturer instructions. The signal was detected using the Genepix 4000 microarray reader and the results were analyzed using the Genepix 3.0 software (Whatman/Schleicher & Schuell).

RNA Interference

EOC cells were transiently transfected with a GFP-expressing plasmid containing silencing RNA (siRNA) directed against MyD88 (psiRNA-hMyD88, Invivogen, San Diego, Calif.). Briefly, $1.5 \times 10^5$ cells were seeded in 60 mm dishes and cultured overnight until 40-60% confluent. Cells were then transfected for 18 h with 2 µg of DNA using Fugene 6 Transfection reagent (Roche Applied Science, Indianapolis, Ind.). Ratio of Fugene to DNA was 3:1. Following transfection, cells were allowed to recover in growth media for 24 h prior to treatment.

MyD88 Transfections

Transfection was performed using a plasmid containing the full-length cDNA (SEQ ID NO:3) of human MyD88 (pUNO-hMyD88, Invivogen), which encodes the amino acid sequence of SEQ ID NO:4. CP70 and A2780 cells were grown in 75 mm² surface tissue culture flasks until they reached 50% confluence. 12 µl of the Fugene 6 Transfection reagent was added into 4 ml of serum-free media for each transfection. After 5 minutes of incubation at room temperature, 1 µg of the plasmid pUNO-hMyD88 was added to the serum-free media containing Fugene 6 Transfection Reagent, and the mixtures were incubated at room temperature for another 15 minutes. The growth media in each flask was discarded, and the corresponding Fugene 6-plasmid-serum-free-media mixture was added and the flasks were incubated overnight at 37° C. 5% $CO_2$. The transfection media was replaced with fresh growth media the second day and the cells were allowed to recover for 24 hours post transfection before treatments.

Laser Capture Microdissection (LCM)

Ovarian cancer specimens (n=24) obtained in the operating room were snap-frozen in liquid nitrogen and stored in cryovials at −80° C. For Laser capture microdissection, a small fraction of tissue was embedded in OCT at −20° C. Eight microns sections were cut with a microtome and fixed on Leica glass foiled PEN-membrane slides. The specimens were fixed in 95% ethanol and H&E stained. Dehydration was performed by immersing the slides in 100% ethanol, followed by Histosolve (Xylene substitute) and air-drying for 10-15 minutes.

Using the Leica Laser Capture Microdissection System (Leica Microsystems MA) 6000 ovarian cancer cells were selected and collected in PCR Eppendorf tubes containing Sample Buffer used for preparation of samples for Western blot analysis. Samples underwent five cycles of thawing and freezing followed by 10 minutes at 95° C. Afterward the samples were stored at −20° C. until used for Western Blot analysis.

Statistical Analysis

Data are expressed as mean±standard deviation (21). Statistical significance ($p<0.05$) was determined using one-way ANOVA with the Bonferonni correction. Survival curve of the patients were done by the method of Kaplan-Meier (22) and the significance of the difference was estimated by log-rank test.

Example 1

EOC Expression of TLR-4 and the Signaling Adapter Protein MyD88

First, Applicants determined whether TLR-4 is expressed in EOC cells. TLR-4 expression was evaluated in paraffin sections of ovarian cancer tissues. Positive immunoreactivity for TLR-4 was observed in the tumor cells, but not in the neighboring non-dysplastic cells. The staining was localized in the cytoplasm as well as on the cell surface. Next, TLR-4 expression was evaluated in EOC cell lines isolated from malignant ovarian ascites and from ovarian cancer tissues. Positive immunoreactivity for TLR-4 was observed in all of the evaluated EOC cell lines. The staining pattern was similar to that observed on the paraffin sections. No staining was observed when mouse IgG1 was used as negative control.

To confirm the specificity of these findings, the expression of TLR-4 by EOC cells and tumors was further evaluated by RT-PCR and Western blot analysis. EOC cells and tumors expressed TLR-4, both at the mRNA and protein level. In addition, the mRNA message for TLR-4 was found to be expressed in a normal ovarian surface epithelium (OSE) cell line immortalized with telomerase (19).

In order to determine whether TLR-4 expressed in EOC cells had the potential to signal and, therefore, be functional, Applicants evaluated expression of the TLR signaling adapter protein, MyD88. Unlike TLR-4, which was ubiquitously expressed by all EOC cell lines and tumors evaluated, the expression of MyD88 was cell line and tumor specific. Furthermore, normal OSE cells, which expressed TLR-4 did not express MyD88.

Applicants also evaluated whether the expression of TLR-4 and MyD88 could be determined in cancer cells isolated with laser microdissector. Ovarian cancer cells were micro-dissected from 8 μM tissue sections using Laser Capture Micro dissector. Cells were collected in sample buffer and TLR-4 and MyD88 expression was evaluated by Western blot.

Example 2

MyD88 Expression is Required for LPS-Induced Tumor Growth

Once the expression of TLR-4 in EOC samples was established, Applicants evaluated the biological function of this receptor and also evaluated the significance of MyD88 status. EOC cell lines expressing MyD88 (MyD88$^+$) and those shown to lack MyD88 (MyD88$^-$) were treated with increasing concentrations of LPS (one of the main ligands for TLR-4) for 24 h and 48 h and cell viability was determined using a cell proliferation assay, i.e., the CELLTITER96® AQueous One Solution Cell Proliferation Assay. A significant increase in cell proliferation was observed at 24 h ($p<0.01$) and 48 h ($p<0.01$) in MyD88$^+$, but not in MyD88$^-$ EOC cells. Thus, LPS induced a time- and dose-dependent increase in cell proliferation in cells expressing MyD88, but not in MyD88– EOC cells. LPS had no effect on viability of OSE cell, which are also negative for MyD88 expression. These results support the dependence of the proliferative effect of LPS in EOC cells on the presence of MyD88.

Example 3

TLR-4 Ligation by LPS Induced Cytokine Production in MyD88 Expressing Cell Lines One of the main characteristics of TLR-4 ligation by LPS in cells of the immune system is the induction of cytokine production, mainly of the pro-inflammatory type. Thus, Applicants' next objective was to evaluate whether TLR-4 ligation by LPS would have a similar effect in EOC cells. Thus, MyD88$^+$ EOC cells were incubated in the presence or absence of 10 μg/ml LPS for 48 h and cytokine secretion was evaluated in the cell-free culture supernatants using a human cytokine array. MyD88$^+$ EOC cells constitutively secreted a wide range of proinflammatory cytokines and chemokines and this secretion was further enhanced by TLR-4 ligation with LPS.

The results from the cytokine array led to the identification of specific cytokines/chemokines that were significantly affected by LPS treatment. To validate these results, Applicants performed ELISA and compared the differential response between MyD88$^+$ and MyD88$^-$ EOC cells. EOC cell lines were treated for 48 h with 10 μg/ml LPS and the levels of GRO-α, MCP-1, and IL-6 were determined. These cytokines were selected because their secretion was shown to be the most significantly affected by LPS treatment. Unstimulated MyD88$^+$ EOC cells constitutively express all the cytokines tested. In addition, TLR-4 ligation significantly induced secretion of GRO-A ($p<0.05$), MCP-1 ($p<0.05$) and IL-6 ($p<0.01$). In contrast, unstimulated MyD88$^-$ EOC cells secreted undetectable or low levels of these pro-inflammatory cytokines, which were not affected by TLR-4 ligation with LPS. These findings suggest that the increased production of pro-inflammatory cytokines in response to LPS was dependent on MyD88 expression in EOC cells.

Example 4

TLR-4 Activates the NF-κB Pathway in MyD88 Expressing EOC Cells

NF-κB is one of the main intracellular pathways mediating the induction of cytokine expression following TLR-4 activation. Therefore Applicants determined if the ligation of TLR-4 induces NF-κB activation in EOC cells. EOC cells were incubated in the presence or absence of LPS (10 μg/ml) for 1, 2 and 4 h and the activation status of NF-κB was determined by Western blot analysis. In MyD88$^+$ EOC cells, the p65 active form of NF-κB was translocated to the nucleus 1 h post-treatment with LPS. This shows that in MyD88$^+$ EOC cells, the ligation of TLR-4 by LPS induces NF-κB activation. Interestingly, constitutive nuclear localization of p65 NF-κB was observed in MyD88$^-$ EOC cells, and its level was not affected by LPS treatment. Therefore, Applicants determined the status of the NF-κ inhibitor, IκB-α, in these cells. Results show IκB-α degradation in MyD88$^+$ cells in response to LPS. In contrast, constitutive degradation of IκB-α was not observed in MyD88$^-$ cells and in addition, no change in its level was observed after LPS treatment. These results are evidence that TLR-4 ligation by LPS results in early phase activation of NF-κB in MyD88$^+$ but not in MyD88$^-$ EOC cells.

Example 5

MyD88 Expression was Associated with Paclitaxel Resistance

Paclitaxel has been reported to be a potential ligand to TLR-4 (23). Since Applicants' results showed that (i) TLR-4 is ubiquitously expressed in all EOC cell lines tested, (ii) MyD88 expression is cell line specific, and (iii) since paclitaxel resistance is a major characteristic of recurrent ovarian cancer, they evaluated whether MyD88 status affects the response of EOC cells to paclitaxel. EOC cells were treated with 2 μM paclitaxel for 24 h and apoptosis was determined by measuring the activity of caspases-3 and -7 using a caspase assay kit CASPASE GLO™ 3/7 Assay. There was a significant increase in caspase-3/7 activity following paclitaxel treatment in MyD88⁻ EOC cell lines. Significant increase in caspase activity was also observed in normal OSE cells following paclitaxel treatment. In contrast, no significant change in caspase-3/7 activity was detected in MyD88⁺ EOC cells. These results are evidence that the MyD88 status of EOC cells determines their apoptotic response to paclitaxel.

Example 6

MyD88 Expression Mediates Paclitaxel-Induced Production of Pro-Inflammatory Cytokines Since the previous results showed that TLR-4 ligation by LPS in MyD88⁺ EOC cells results in increased cytokine secretion, Applicants then determined if TLR-4 ligation by paclitaxel would induce the same type of response. MyD88⁺ and MyD88⁻ EOC cells were treated with increasing concentrations of paclitaxel for 24 h, 48 h, and 72 h and levels of IL-6 secretion were determined by ELISA. In MyD88⁺ EOC cell lines, paclitaxel induced a significant increase in IL-6 production in a dose- and time-dependent manner ($p<0.01$). In contrast, paclitaxel treatment did not affect IL-6 levels in MyD88⁻ EOC cell lines.

To further characterize the effect of paclitaxel and LPS on the secretion of several cytokines and chemokines in MyD88⁺ and MyD88⁻ EOC cells, Applicants used a high throughput microarray system (Whatman/Schleicher & Schull) to measure the levels of IL-6, IL-4, IL-8, IL-12, RANTES, and IFN-γ. Cytokine secretion was measured in the supernatants of EOC cells following 48 h incubation with either LPS (10 μg/ml) or paclitaxel (20 μM). MyD88⁺ EOC cells displayed constitutive secretion of the pro-inflammatory cytokines, IL-6, IL-8 and RANTES, and treatment with LPS or paclitaxel resulted in increased secretion of these pro-inflammatory cytokines. In contrast, MyD88⁻ EOC cells showed neither constitutive secretion nor LPS- or paclitaxel-induced TL-6, IL-8 or RANTES secretion. Interestingly, neither MyD88⁺ nor MyD88⁻ EOC cells secreted detectable levels of IL-4, IL-12 and IFN-γ, with or without treatment with either LPS or paclitaxel.

Example 7

Expression of MyD88 in EOC Cells is Necessary for IL-6 Production

In order to confirm that in MyD88⁺ EOC cells, the ligation of TLR-4 by either LPS or paclitaxel induces the production of cytokines, Applicants inhibited its expression in MyD88⁺ R182 EOC cells using RNA interference technology. As shown above, wild type (wt) R182 cells produce high levels of IL-6 in response to both LPS (10 μg/ml) and paclitaxel (2 μM). However, following the inhibition of MyD88 expression by RNAi, treatment with LPS or paclitaxel resulted in decreased IL-6 secretion. These findings confirmed that the cytokine response in EOC cells following LPS and paclitaxel treatment involves signaling through MyD88.

Example 8

Induction of MyD88 Expression in EOC Cells Reverses Chemosensitivity to Paclitaxel Because Applicants observed a positive correlation between MyD88 expression and resistance to paclitaxel-induced apoptosis, their next objective was to determine whether the induction of MyD88 expression in EOC might confer resistance to paclitaxel. Therefore, they induced the expression of MyD88 in A2780 and CP70 EOC cells, both MyD88⁻ and paclitaxel-sensitive, by transient transfection with a plasmid vector containing the full-length cDNA of MyD88 (pUNO-hMyD88). After 24 h of transfection, the cells were either left untreated or treated with 2 μM paclitaxel for 48 h and caspase-3/7 activity was determined. A significant increase in caspase-3/7 activity was observed in wt cells following paclitaxel treatment. In contrast, no changes in caspase-3/7 activity were observed in cells transfected with pUNO-hMyD88. These findings show that MyD88 expression contributes to paclitaxel chemo-resistance.

Applicants also determined whether the expression of MyD88 confers resistance that is specific to paclitaxel. Wild-type (wt) A2780 EOC cells (carboplatin sensitive) and A2780 EOC cells transfected with MyD88 were treated with 100 μg/ml carboplatin or 2 μM paclitaxel for 48 hours. Apoptosis was determined by measuring caspase-3/7 activity. Wildtype A2780 cells showed significant increase in caspase-3/7 activity following treatment with carboplatin or paclitaxel. Upon the introduction of MyD88, the cells retained its sensitivity to carboplatin, but not paclitaxel. These results are evidence that the protective effect of MyD88 is specific for paclitaxel-induced apoptosis.

Example 9

TLR-4 Ligation by Paclitaxel Induces the Expression of Anti-Apoptotic Proteins

TLR-4 ligation through NF-κB and inflammatory molecules promotes cell survival by the induction of the expression of anti-apoptotic proteins (24, 25). The expression of X-linked inhibitor of apoptosis (XIAP), a major inhibitor of caspase-3 and 9, and the expression of Akt has been associated with tumor growth and chemoresistance in ovarian cancer cells (26-28). Therefore, Applicants evaluated the expression of XIAP and phosphorylated Akt (pAkt) following paclitaxel treatment in MyD88⁺ cells. A significant increase in pAkt was observed 4 h after treatment with paclitaxel. Similarly, XIAP levels increased 2 h post-treatment. In contrast, no change on the levels of total Akt was observed.

Example 10

Correlation Between MyD88 Expression in Ovarian Cancer Tissues and Patients' Progression Free Survival In order to determine whether the in vitro findings have clinical relevance, Applicants performed a pilot retrospective study to analyze MyD88 expression in tissues obtained from patients with stage IIIC ovarian cancer (n=12) and determine whether there is a correlation between MyD88 expression and progression free survival. Tissue collection was performed prior to chemotherapy and the expression of MyD88 in ovarian cancer tissues was determined by western blot analysis. All patients received six cycles of paclitaxel/carboplatin regimen after surgery. The mean time to recurrence for patients with tumors that expressed MyD88 was 23 months (n=5). However, the mean time to recurrence for patients with tumors that did not express MyD88 was 42 months (n=7). Patients whose tumors did not express MyD88 had a statistically significant improved progression free interval compared to patients whose tumors expressed MyD88 ($p=0.03$).

Discussion

Substantial evidence indicates that bacterial- and viral-induced inflammatory processes can mediate tumorigenesis. Described herein is a specific defense mechanism used by the innate immune system, which cancer cells have imitated and adapted to generate proinflammatory cytokines, leading to their own proliferation and survival. Described herein is: 1) the expression of TLR-4 in EOC cells; 2) the induction of tumor growth by TLR-4 ligation in MyD88+ EOC cells; 3) the production of chemokines and cytokines by MyD88+ EOC cells upon TLR-4 ligation; and 4) chemo-resistance to paclitaxel mediated by the expression of MyD88.

It has been observed in animal studies that surgical removal of a primary tumor is often followed by rapid growth of previously dormant metastases and LPS has been suggested to be responsible for this effect (29). Indeed, Balb/c mice receiving a tail vein injection of 4T1 mouse mammary carcinoma cells showed an increase in lung metastases following LPS injection (30). LPS is recognized by TLR-4, which is expressed by the cells of the innate immune system. Following its ligation, it has been shown to induce NFκB activation, cytokines/chemokines production and inflammation (14).

TLRs represent a main receptor pathway, which can induce the expression of pro-inflammatory cytokines (15). TLRs are widely expressed by cells of the immune system and, in response to microbial products or stress factors, initiate an inflammatory process (10). In addition, TLRs have been described in non-immune cells, such as mucosal epithelium and trophoblast cells (20, 31). Similar to immune cells, the ligation of TLRs in non-immune cells results in the expression and secretion of pro-inflammatory cytokines (20). Here, Applicants describe the presence of TLR-4 in all EOC cells tested and the differential expression of MyD88. Applicants showed that in MyD88+ EOC cells, ligation of TLR-4 by LPS enhances cell proliferation and induces the production of chemokines and pro-inflammatory cytokines. Interestingly, unstimulated MyD88+ cells constitutively secrete cytokines/chemokines. This suggests the presence of endogenous ligands of TLRs (e.g., apoptotic bodies, cellular debris from necrotic cells), which can also act through TLR-4 or other TLRs, which are also present in EOC cells (our unpublished data).

One of the main cytokines induced in EOC cells following LPS stimulation is IL-6. In addition, following TLR-4 ligation, these cells secreted the chemokines, MCP-1 and GRO-α. It is now well documented that chemokines can dramatically alter the neoplastic process, not only by recruiting leukocytes that will enhance the inflammatory environment, but also by having a direct effect on nearby stromal and neoplastic cells (32). The induction of these chemokines by TLR-4 activation may, therefore, help to recruit inflammatory cells as well as to enhance tumor growth and neoplastic progression. Melanoma is one example in which chemokines have been shown to exert autocrine control over neoplastic proliferation (33, 34). Blocking GRO-α activity on the CXCR2 receptor attenuates melanoma cell proliferation in vitro, whereas over expression of GRO-α and GRO-α enhances tumor colony formation and tumorogenicity in nude mice (34-36). Here, ligation of TLR-4 by LPS induced a significant increase in GRO-α secretion, which may provide the stimuli for the proliferative effect observed on EOC cells following LPS treatment. Furthermore, the presence of pro inflammatory cytokines and chemokines has been described as predictors of poor prognosis (37).

As described herein Applicants have identified a subgroup of epithelial ovarian cancer (EOC) cells that express the protein Myeloid Differentiation Protein 88 (MyD88). MyD88 is an adaptor protein that is required for Toll-like receptor (TLR) signaling, a signaling pathway involved in inflammatory response to bacterial and viral products. EOC cells that express MyD88 constitutively secrete pro-inflammatory cytokines (IL-6, IL-8, GROα); exhibit high levels of NF-κB; and are resistant to the taxane paclitaxel, which is a known TLR-4 ligand. Upon TLR-4 ligation with either LPS or paclitaxel, these cells secrete higher levels of pro-inflammatory cytokines and, more importantly, proliferate in culture. Applicants hypothesized that MyD88 is a specific marker for paclitaxel resistance and is required for paclitaxel-induced cell growth in EOC cells. The objective of the work described in this example was to develop an optimized method that can detect MyD88 expression in ovarian cancer tumors and thus provide a way for MyD88 as a biomarker for selection of therapy.

Proteomics has emerged as an important tool to study biological processes in both physiological and pathological circumstances. Identification of specific proteins as biomarkers for a disease or condition may be used for diagnosis and/or therapy. Currently however, no optimized method exists that can sensitively detect ovarian cancer biomarkers from tumor tissue prior to initiation of therapy. A limiting factor in the discovery and analysis of potential marker from tumor samples are the "contaminating" signals originating from normal cells, including immune cells, that are infiltrating the tumor. Described herein is a novel approach for the detection of protein expression in a small sample of cancer cells, as exemplified by epithelial ovarian cancer cells dissected by LCM. Furthermore, demonstrated herein is proof that MyD88 expression in LCM-dissected ovarian cancer cells is a marker for paclitaxel resistance.

Applicants observed differential response to LPS by EOC cells, which was due to the expression of the TLR intracellular signaling molecule, MyD88. In the presence of MyD88, treatment with LPS results in the nuclear localization of NF-κB, increase cell proliferation, and cytokine/chemokine production. These results provide preliminary evidence of the involvement of NF-κB in TLR-4-MyD88 signaling pathway in EOC cells. However, the exact downstream signaling pathway after TLR-4-MyD88 activation still remains to be determined.

In the absence of MyD88, treatment with LPS failed to induce NF-κB translocation to the nucleus and had no effect on cellular proliferation nor on cytokine/chemokine production. Interestingly however, the MyD88− A2780 EOC cell line constitutively express nuclear p65 NF-κB, yet does not constitutively express any of the pro-inflammatory cytokines observed in MyD88+ cells. These results suggest that the impact of NF-κB on cancer cells may be cell-type specific and the final output of NF-κB activation, e.g. cytokine production, is the determining factor in tumor progression and differentiation. The significance of this constitutive NF-κB nuclear localization in these cells, which is not related to the production of pro-inflammatory cytokines, is under investigation in our laboratory.

Differential response was also observed in EOC cells in response to paclitaxel. MyD88+ EOC cells responded to paclitaxel in similar manner as they did with LPS: they produced and secreted pro-inflammatory cytokines. In addition, these cells did not undergo apoptosis in response to paclitaxel. This is in contrast to MyD88− cells, which underwent apoptosis and did not secrete cytokine/chemokine in response to paclitaxel.

Studies in mice by Ding et al showed that similar to LPS, treatment with paclitaxel activates murine macrophages and induces the secretion of inflammatory cytokines, including TNFα, IL-6 and IL-8. This effect of paclitaxel was demonstrated to be both TLR-4 and MyD88 dependent (38) (23). These results are supported by the in vivo observation showing a correlation between expression of MyD88 and progression free survival. Although only a small number of patients was evaluated, the data indicate that the expression of MyD88 correlates with a poor survival.

Applicants also demonstrate that in MyD88+ EOC cells, TLR-4 ligation is able to induce the activation of the Akt survival pathway and enhance the expression of the anti-apoptotic protein XIAP. Both proteins have been shown to be highly expressed in ovarian cancer and are linked to the develop of chemoresistance (17, 27, 39). Therefore, in MyD88+ EOC cells, the pro-apoptotic effect of paclitaxel is overcome by the induction of the anti-apoptotic proteins (pAKT and XIAP) following TLR-4 ligation. Therefore, in these cells, treatment with paclitaxel does not induce apoptosis but induces the secretion of cytokines/chemokines. The correlation between TLR-4-MyD88 signaling and the upregulation of pAkt and XIAP remains to be determined. NF-κB may be a link between these pathways.

During the past twenty years multiple combinations of cytotoxic chemotherapeutics have been evaluated in patients with recurrent ovarian cancer. The work described herein provides new insight into a molecular mechanism that links inflammation and neoplastic development/progression. It suggests that an active TLR-4-MyD88 signaling pathway is a risk factor for developing cancer and a novel target for the development of bio-modulators aimed at reversing chemoresistance to paclitaxel.

REFERENCES FOR EXAMPLES 1-10

1. Beachy P A, Karhadkar S S, Berman D M, Nature 2004; 431(7007):402.
2. Balkwill F, Coussens L M, Nature 2004; 431(7007):405-6.
3. Coussens L M, Werb Z, Nature 2002; 420(6917):860-7.
4. Giudice L C, Kao L C, Lancet 2004; 364(9447):1789-99.
5. Riman T, Nilsson S, Persson I R, Acta Obstet Gynecol Scand 2004; 83(9):783-95.
6. Sekizawa A, Amemiya S, Otsuka J, et al., Med Electron Microsc 2004; 37(2):97-100.
7. Robinson S C, Coussens L M, Adv Cancer Res 2005; 93:159-87.
8. de Visser K E, Coussens L M, Cancer Immunol Immunother 2005; 54(11):1143-52.
9. Anderson K V, Bokla L, Nusslein-Volhard C, Cell 1985; 42(3):791-8.
10. Medzhitov R, Nat Rev Immunol 2001; 1(2):135-45.
11. Medzhitov R, Janeway C A, Jr., Cell 1997; 91(3):295-8.
12. Takeuchi O, Akira S, Int Immunopharmacol 2001; 1(4):625-35.
13. Medzhitov R, Janeway C A, Jr., Science 2002; 296(5566):298-300.
14. Akira S, J Biol Chem 2003; 278(40):38105-8.
15. Akira S, Takeda K, Nat Rev Immunol 2004; 4(7):499-511.
16. Behrens B C, Hamilton T C, Masuda H, et al., Cancer Res 1987; 47(2):414-8.
17. Kamsteeg M, Rutherford T, Sapi E, et al., Oncogene 2003; 22(17):2611-20.
18. Flick M B, O'Malley D, Rutherford T, et al., J Soc Gynecol Inv 2004; 11:252-9.
19. Alvero A B, Fishman D A, Qumsiyeh M B, Garg M, Kacinski B M, Sapi E, J Soc Gynecol Investig 2004; 11(8):553-61.
20. Abrahams V M, Bole-Aldo P, Kim Y M, et al., J Immunol 2004; 173(7):4286-96.
21. O'Dwyer P J, Moyer J D, Suffness M, et al., Cancer Res 1994; 54:724-9.
22. Kaplan E, Meier P., J Amm Stat As 1958; 55:457-81.
23. Byrd-Leifer C A, Block E F, Takeda K, Akira S, Ding A, Eur J Immunol 2001; 31 (8):2448-57.
24. Schmitz I, Kirchhoff S, Krammer P H, Int J Biochem Cell Biol 2000; 32(11-12):1123-36.
25. Nakanishi C, Toi M, Nat Rev Cancer 2005; 5(4):297-309.
26. Yuan Z Q, Feldman R I, Sussman G E, Coppola D, Nicosia S V, Cheng J Q, Biol Chem 2003; 278(26):23432-40.
27. Dan H C, Sun M, Kaneko S, et al., J Biol Chem 2004; 279(7):5405-12.
28. Dan H C, Jiang K, Coppola D, et al., Oncogene 2004; 23(3):706-15.
29. Pidgeon G P, Harmey J H, Kay E, Da Costa M, Redmond H P, Bouchier-Hayes D J, Br J Cancer 1999; 81(8):1311-7.
30. Harmey J H, Bucana C D, Lu W, et al, Int J Cancer 2002; 101(5):415-22.
31. Abrahams V M, Mor G, Placenta 2005; 26(7):540-7.
32. Vicari A P, Caux C, Cytokine Growth Factor Rev 2002; 13(2):143-54.
33. Richmond A, Thomas H G, J Cell Physiol 1986; 129(3): 375-84.
34. Richmond A, Fine R, Murray D, Lawson D H, Priest J H, J Invest Dermatol 1986; 86(3):295-302.
35. Metzner B, Barbisch M, Bachmann F, Czech W, Norgauer J, J Invest Dermatol 1996; 107(4):597-602.
36. Norgauer J, Metzner B, Schraufstatter I, J Immunol 1996; 156(3): 1132-37.
37. McMillan D C, Canna K, MeArdle C S, Br J Surg 2003; 90(2):215-9.
38. Ding A H, Porteu F, Sanchez E, Nathan C F, Science 1990; 248(4953):370-2.
39. Sapi E, Chen W, O'Malley D, et al, Anti-Cancer Drugs 2004; 14:567-78.

Materials and Methods

The following materials and methods were used in Examples 11-13.

Patients and Samples Preparation

Ovarian cancer tissue samples were collected from advanced stage ovarian cancer patients at the time of surgery. All patients signed consent forms and the use of patient samples was approved under Yale University's Human Investigations Committee (HIC #10425).

Tissues were prepared in small aliquots and snap-frozen in liquid $N_2$. All samples were stored in cryovials at −80° C. until future use.

Antibodies and Reagents for Immunocytochemistry (IHC)

Albumin from bovine serum/BSA was purchased from Sigma Aldrich, St. Louis, Mo.

The primary antibody was Dako OV-TL mouse monoclonal cytokeratin-7 from Dakocytomation, Carpinteria, Calif. Primary antibody dilution was 1:150 in 1% BSA mixed in wash buffer. The secondary antibody used was biotinylated anti-mouse IgG (H+L) made in horse from Vector Laboratories, Burlingame, Calif. Dilution was 1:200 in 1% BSA/wash buffer. As detection reagent we used Streptavidin-HRP Conjugate from Zymed, San Francisco, Calif., in a 1:300 dilution.

Antibodies and Reagents for Western Blot Analysis

Primary antibodies used for Western blot analysis were rabbit polyclonal anti-human and mouse antibody to MyD88 (dilution 1:1000 in PBS-T/1% FFPM) from eBioscience (San Diego, Calif.), mouse monoclonal anti-human antibodies to FasL/CD95L (dilution 1:10,000 in PBS-T/1% FFPM) from BD Biosciences (San Jose, Calif.), mouse monoclonal anti-human antibodies to hIAL/XIAP (dilution 1:10,000 in PBS-T/1% FFPM) from BD Biosciences PharMingen (San Diego, Calif.). Secondary peroxidase-conjugated antibodies, anti-rabbit IgG (H+L) made in goat and anti-mouse IgG (H+L) made in horse, were purchased from Vector Laboratories (Burlingame, Calif.).

Slide Preparation

In preparation for Laser capture microdissection a 5×5 mm tissue sample was embedded in OCT at −20° C. Eight-micron sections were cut with the microtome and collected on Leica glass-foiled PEN-membrane slides. The slides were fixed in 95% ethanol for 5 minutes and stained with H&E for 30 seconds at RT, followed by washing in ddH$_2$O for 30 seconds. Dehydration is required for successful Laser microdissection and this was accomplished by immersing the slides in 95% ethanol and then in Histosolve, a xylene substitute (Shandon, Inc., Pittsburgh, Pa.), 15 minutes each. The slides were air dried at RT for 15 minutes. Following dehydration, to prevent protein degradation, the samples were either used immediately for microdissection or they were stored in air-tight plastic wrapping at −20° C.

Immunohistochemistry for Laser Microdissection

Eight-micron sections were cut with the microtome, collected on Leica glass-foiled PEN-membrane slides and fixed in 95% ethanol for 5 minutes as described above. The slides were then placed in a staining dish with 0.1% H$_2$O$_2$ in 0.1M PB for 10 minutes to quench for endogenous peroxidase activity and then washed in wash buffer 3 times. Wash buffer was prepared by adding 0.01% Triton X-100 (Sigma Aldrich, St. Louis, Mo.) to 0.1M PB. The area around the tissue sections was scored with a Pap pen to limit the amount of antibodies and reagents used. All steps occurred at room temperature with the slides placed in a moisture chamber to keep the tissue from drying out during the procedure. To block for non-specific background, 100-200 μl of 3% BSA made in wash buffer were added to the circumscribed areas and incubated for 20 minutes in the moisture chamber. Next, the primary antibody was incubated for 2 hours followed by washing with wash buffer (each wash is 2-3 minutes×3), the specimens were incubated with Biotin labeled secondary antibody for 30 minutes. After this incubation, the slides were washed once with wash buffer then twice with 0.1M Tris (pH 7.5). The tissue was incubated with Streptavidin-HRP conjugate for 30 minutes and then washed with 0.1 M Tris 3 times. The color was developed with DAB (2.5 mg DAB in 5 ml 0.1 M Tris). Twenty five μl of 0.03% H$_2$O$_2$ were added to the chromogen just before use. At the end of the procedure the slides were washed with double distilled water and counter-stained with Mayer's hematoxylin (Sigma Aldrich, St. Louis, Mo.). The specimens were dehydrated and then stored as described above.

Laser Microdissection for Western Blot Analysis

The slides were placed inverted into the holder of a Leica AS LMD Laser Microdissection System with the side containing the tissue facing down (non-contact method). Tumor cells were selected according to their morphology for H&E stained samples or according to their immunoreactivity for CK-7 stained samples. Dissected cells were collected in the cup of 0.5 ml Eppendorf tubes containing 35 μl sample buffer (2.5% SDS, 10% glycerol, 5% β-mercapto-ethanol, 0.15M Tris (pH=6.8) and 0.01% bromophenol blue). After a short centrifugation, lysis of the cells was achieved by submitting the samples to 5 cycles of freezing (liquid N$_2$) and thawing (95° C.) followed by boiling for 5 minutes, centrifuged again for 2 minutes and then stored at −80° C. until further use.

All procedures were carried out in a timely manner to minimize the activity of proteases. For H&E stained tissues, the interval from tissue frozen section cutting to cell dissection and lysis was under 1 hour while immunostained (CK-7 or CD45) stained specimens required approximately 4 hours.

Western Blot Analysis

Proteins were resolved under reducing conditions on 12% SDS-PAGE gels and then transferred onto polyvinylidene difluoride paper (NEN Life Sciences, Boston, Mass.) (5). Membranes were blocked at room temperature for 1 hour with 5% FFPM in PBS/0.05% Tween 20 (PBS-T). After three washes for 10 minutes, each with PBS-T, membranes were incubated overnight at 4° C. with the primary antibody in PBS-T/1% FFPM. After incubation with the primary antibody, membranes were washed three times with PBS-T and then incubated at room temperature with the appropriate secondary antibody conjugated to peroxidase (Vector Laboratories) in PBS-T/1% FFPM. After three washes for 10 minutes each with PBS-T and three washes for 10 minutes each with distilled water, the peroxidase-conjugated antibody was detected by enhanced chemoluminescence (PerkinElmer Life Sciences, Boston, Mass.). The signal intensity was analyzed using a Kodak digital imaging analysis system Kodak Image Station 4000MM) and Kodak Molecular Imaging Software (Scientific Imaging Kodak Company).

Example 11

Protein Detection in Isolated Cells

Results demonstrated that protein expression can be detected by Western blot analysis in microdissected cells obtained from ovarian tumor samples that were snap-frozen in liquid N2. Increasing number of cells were microdissected with a maximum of 8,000 cells and a minimum of 100 cells from 8 μm ovarian cancer sections. These were analyzed for the expression of MyD88 and other cancer-related proteins, such as XIAP and FasL. A strong signal for MyD88 expression was observed in samples containing 8,000 and 5,000 microdissected cells; no signal was detected for samples containing fewer than 1,000 cells.

In order to determine whether the sensitivity of the assay remains similar for different proteins, Applicants evaluated the expression of XIAP and FasL using the same number of cells as for MyD88. In contrast to MyD88, XIAP and FasL expression is detected in samples containing as few as 1000 and 100 cells, respectively.

Whether sample thickness affects the signal detected by Western blot was also evaluated. Although increasing the section thickness increased the amount of protein, it affected cutting time and rendered dissection extremely difficult. Therefore, the method was standardized to 8 μm sections. This allows a quick dissection and provides enough protein to be detected by Western blot.

As a result, Applicants demonstrated that fresh-frozen tissue is a suitable material for LCM. They showed that proteins involved in the apoptolic cascade and chemoresistance of EOC cells can be accurately detected by, for example, snap freezing tumor specimens in liquid nitrogen, and staining specimens (e.g., 8 μm thick specimens to facilitate selection of pure tumor cells; identifying target cells, based on their immunostaining and collecting target cells (e.g., with the LCM system); and lysing collected target cells, followed by analysis for protein content/makeup (e.g., by Western blot or Luminex multiplex analysis).

Example 12

MyD88 Expression is Cell-Type Specific

Tumors are heterogeneous tissues containing normal supporting cells, immune cells and cancer cells. Immune cells infiltrate the stroma and may "contaminate" the protein profile of the tumor sample. Indeed, when Applicants analyzed MyD88 expression in H&E stained samples without using appropriate markers for cell type identification, they found that MyD88 was expressed in all samples. The explanation for these results is that the immune cells present in the tumor tissue and surrounding the cancer cells express MyD88. In an H&E stained sample, the selection of specific cells based on their morphology alone is not sufficient to identify intratumoral infiltrated cells. An advantage of the LCM is that it affords the possibility of selecting a specific group of cells based on the expression of cellular markers. Therefore, Applicants' next objective was to determine whether immunohistochemistry staining affects the detection of proteins in microdissected samples. Thus, they compared the sensitivity of protein detection of cells obtained from H&E stained samples with cells obtained from immuno-stained samples. Tumor tissues were immuno-stained with antibodies for cytokeratin 7 (epithelial marker) or CD45 (pan-leucocyte marker). Specific staining for cytokeratin 7 and CD45 was observed in these frozen sections. Comparison of MyD88 and XIAP expression in cells obtained from these two preparations, showed no difference in the signal intensity between the two groups, suggesting that the process of IHC does not affect the samples' integrity. After establishing that IHC does not affect protein detection, Applicants evaluated MyD88 expression in ovarian cancer samples after staining for CD45 (pan-leukocyte antigen). Assessment of only cancer cells (CD45 negative cells), avoiding immune cells (CD45 positive cells), showed that MyD88 was differentially expressed in tumors from different patients with identical pathological diagnoses.

Example 13

Clinical Correlation Between MyD88 Expression and Survival/Progression Free Interval Applicants evaluated 20 tumor samples from patients with epithelial ovarian cancer. Eleven out of twenty tumors were MyD88 positive and nine tumors were MyD88 negative.

From the MyD88 positive tumors, 7/11 were obtained at the time of initial surgery from patients who received neoadjuvant chemotherapy with carboplatin and paclitaxel. These patients had persistent or progression of disease during neoadjuvant chemotherapy. Even after neoadjuvant chemotherapy and optimal tumor debulking, these patients failed postoperative chemotherapy. Their progression-free interval was zero and four patients died of disease in less than 1 year. In this group, mean survival was 16 months.

From the MyD88 negative tumor samples, 5/7 were obtained at the time of initial surgery from patients with poorly differentiated serous papillary adenocarcinomas. Three patients were stage IIIC, one was stage IIIB, and one was stage IIC. In this group all patients were treated with carboplatin and paclitaxel and the mean progression-free interval was 35 months. The mean overall survival in this group was 45 months and three patients are alive at the time of this report. Four of eleven MyD88 positive tumors were obtained from patients with recurrent disease who underwent optimal secondary cytoreductive surgery. All four patients (two with recurrent stage IC, one with recurrent stage IIA, and one with recurrent stage IIC) received carboplatin and paclitaxel. Their mean progression-free interval after completion of chemotherapy was 3 months.

Four MyD88 negative tumor samples were obtained from patients with recurrent disease at the time of the secondary cytoreduction. Postoperatively, these patients were treated with paclitaxel and carboplatin combination chemotherapy. One patient with stage IIIC recurred 33 months after primary treatment and one patient with stage IVA recurred 20 months after primary treatment. Mean progression-free interval in this group was 14 months.

Figure 1:
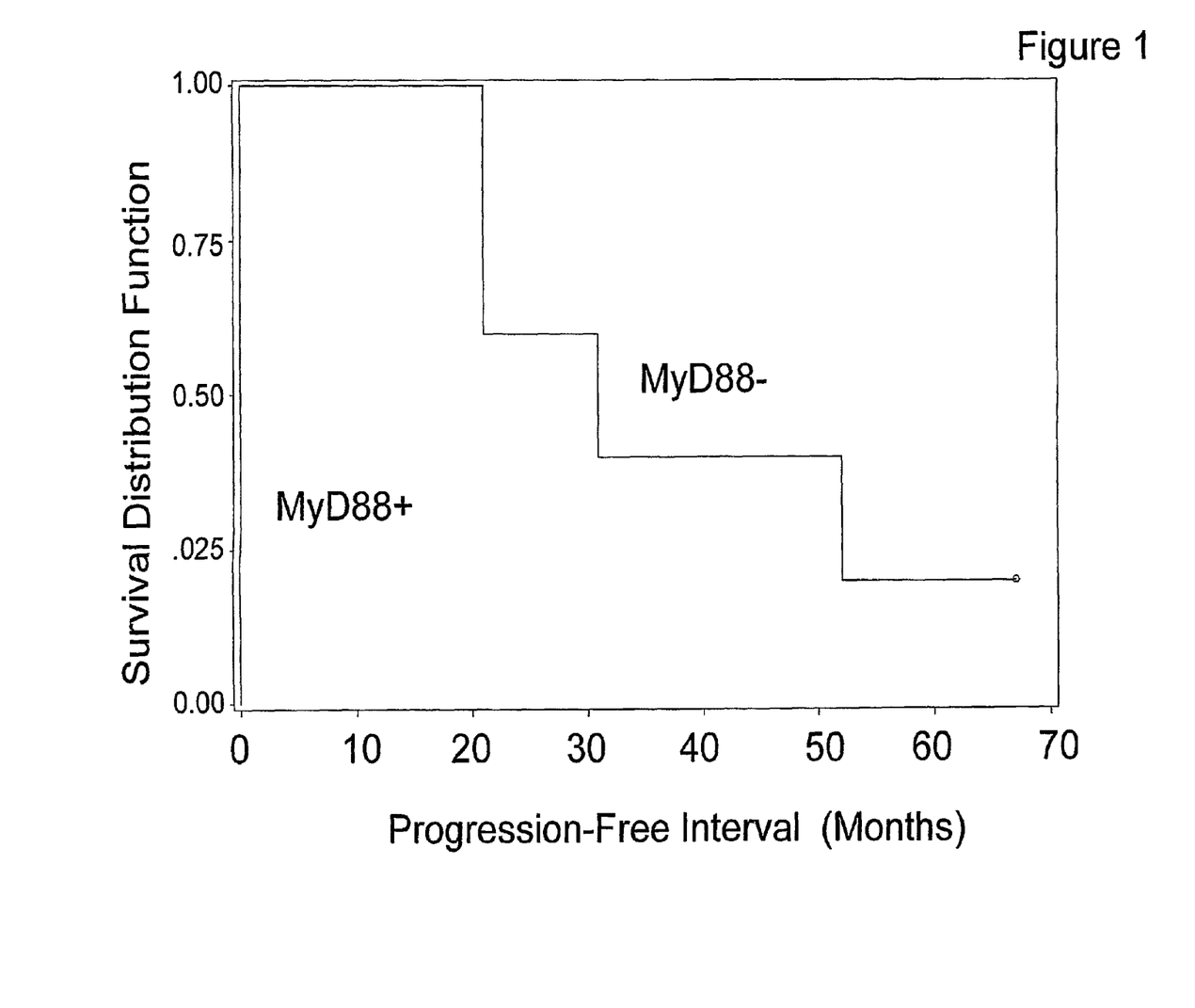
FIG. 1: Mean progression-free interval was zero for patients with MyD88+ tumors (n=7) and 35 months for patients with MyD88− tumors (n=5) treated with carboplatin and paclitaxel. This difference was statistically significant (log rank statistical test p=0.009).
Figure 2:
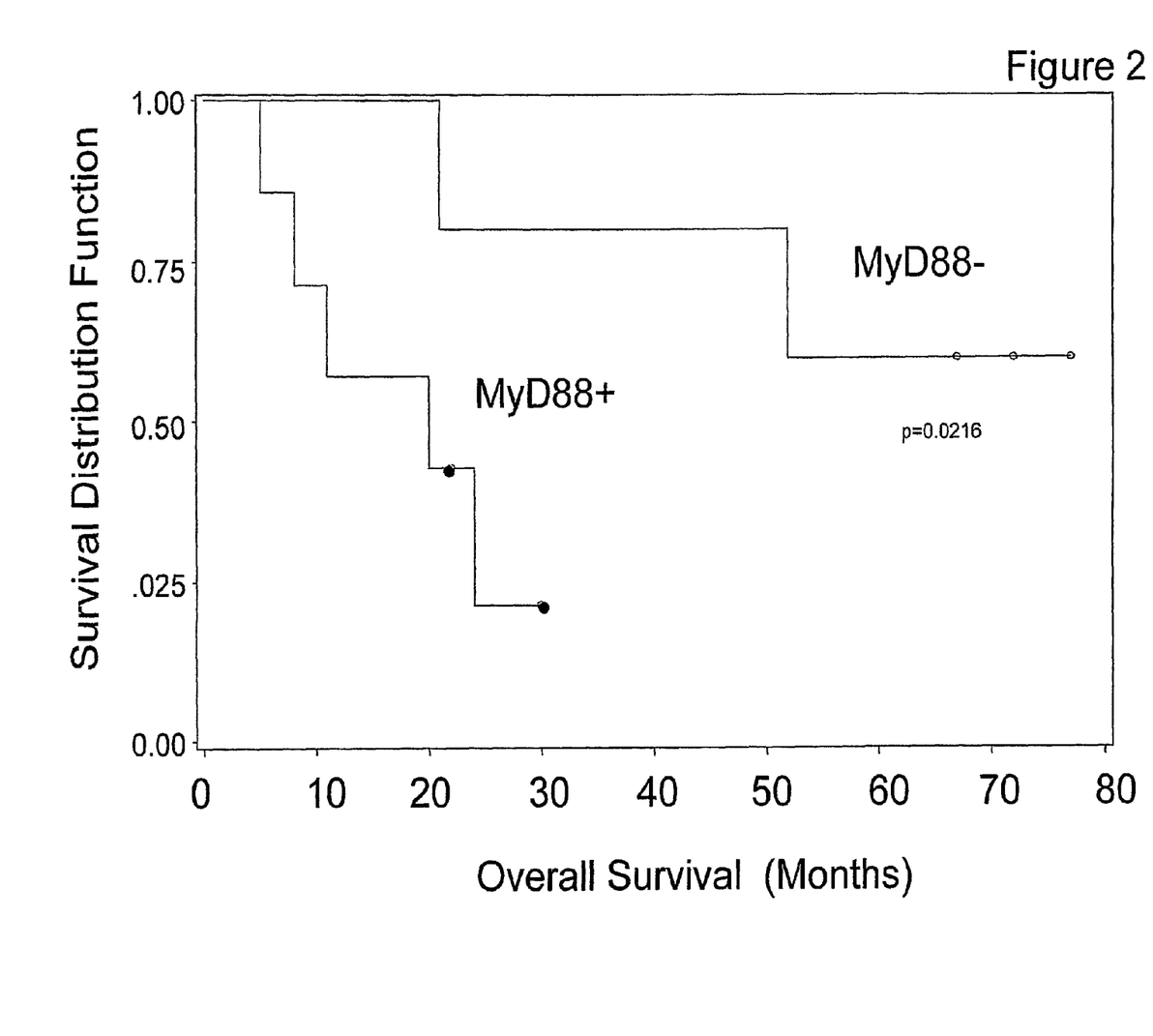
FIG. 2: Overall survival according to the MyD88 status of the analyzed tumors shows divergent Kaplan-Meier curves and was statistically significant (−2 log likelihood ratio test p=0.022).

A statistical significant correlation between assay prediction of response and progression-free interval (PFI) was observed in all these cases. Furthermore, patients who had MyD88 negative tumors responded better to treatment and had a significantly longer survival when compared with the patients who had MyD88 positive tumors (FIGS. 1 and 2).

REFERENCES FOR EXAMPLES 11-13

1. Schwartz P E. Current diagnosis and treatment modalities for ovarian cancer. *Cancer Treat Res* 2002; 107:99-118.
2. Kelly M G, Alvero A B, Chen R, Silasi D A, Abrahams V M, Chan S, et al. TLR-4 signaling promotes tumor growth and paclitaxel chemoresistance in ovarian cancer. *Cancer Res* 2006; 66(7):3859-3868.
3. Ding Y, Xu L, Chen S, Jovanovic B D, Helenowski I B, Kelly D L, et al. Characterization of a method for profiling gene expression in cells recovered from intact human prostate tissue using RNA linear amplification. *Prostate Cancer Prostatic Dis* 2006
4. Matsuzaki S, Canis M, Pouly J L, Botchorishvili R, Dechelotte P J, Mage G. Differential expression of genes in eutopic and ectopic endometrium from patients with ovarian endometriosis. *Fertil Steril* 2006; 86(3):548-553.
5. Alvero A B, O'Malley D, Brown D, Kelly G, Garg M, Chen W, et al. Molecular mechanism of phenoxodiol-induced apoptosis in ovarian carcinoma cells. *Cancer* 2006; 106(3): 599-608.
6. Asselin E, Mills G B, Tsang B K. XIAP regulates Akt activity and caspase-3-dependent cleavage during cisplatin-induced apoptosis in human ovarian epithelial cancer cells. *Cancer Res* 2001; 61(5):1862-1868.
7. Holcik M, Gibson H, Komeluk R G. XIAP: apoptotic brake and promising therapeutic target. *Apoptosis* 2001; 6(4): 253-261.
8. Sapi E, Chen W, O'Malley D, Hao X, Dwipoyono B, Garg M, et al. Resistance of Ovarian Cancer Cells to Docetaxel is XIAP Dependent and Reversible by Phenoxodiol. *Anti-Cancer Drugs* 2004; 14:567-578.
9. Gutierrez L, Eliza M, Niven-Fairchild T, Naftolin F, Mor G. The Fas/Fas-Ligand system: A mechanism for immune evasion in human breast carcinomas. *Breast Cancer Research and Treatment* 1999; 54(3):245-253.
10. Abrahams V, Straszewski S, Kamsteeg M, Hanezaruk B, Schwartz P, Rutherford T, et al. Epithelial Ovarian Cancer secrete functional Fas Ligand. *Cancer Res* 2003; 63:5573-5581.

The invention claimed is:

1. A method of assessing responsiveness of a human cancer cell to a plant alkaloid, comprising determining whether the cancer cell expresses a human Myeloid Differentiation Protein 88 (MyD88$^+$) or does not express the human Myeloid Differentiation Protein 88 (MyD88$^-$), wherein if the cancer cell is MyD88$^+$, it is resistant to the plant alkaloid and if the cancer cell is MyD88$^-$, it is sensitive to the plant alkaloid, and wherein the plant alkaloid is a taxane.

2. The method of claim 1, wherein the taxane is paclitaxel or docetaxel.

3. The method of claim 1, wherein the cancer cell is an ovarian cancer cell, a breast cancer cell, a head cancer cell, a neck cancer cell, a prostate cancer cell, a non-small cell lung cancer cell, a small cell lung cancer cell, a bladder cancer cell, a stomach cancer cell, or a Kaposi's sarcoma cell.

4. The method of claim 3, wherein the cancer cell is an epithelial ovarian cancer cell.

5. A method of assessing sensitivity or resistance of a human cancer cell to chemotherapy with a plant alkaloid, comprising assaying expression of a human Myeloid Differentiation Protein 88 (MyD88) in the cancer cell, wherein the cancer cell is sensitive to chemotherapy with the plant alkaloid if the cancer cell does not express the human MyD88 and the cancer cell is resistant to chemotherapy with the plant alkaloid if the cancer cell expresses the human MyD88, and wherein the plant alkaloid is taxane.

6. The method of claim 5, wherein the taxane is paclitaxel or docetaxel.

7. The method of claim 5, wherein the cancer cell is an ovarian cancer cell, a breast cancer cell, a head cancer cell, a neck cancer cell, a prostate cancer cell, a non-small cell lung cancer cell, a small cell lung cancer cell, a bladder cancer cell, a stomach cancer cell, or a Kaposi's sarcoma cell.

8. The method of claim 5, wherein the cancer cell is an epithelial ovarian cancer cell.

9. The method of claim 1, wherein determining whether the cancer cell expresses the human MyD88 or does not express the human MyD88 is carried out by detecting the presence or absence of the human MyD88 in the human cancer cell, detecting the quantity of the human MyD88 in the human cancer cell, or detecting nucleic acid that encodes the human MyD88 in the human cancer cell.

10. The method of claim 5, wherein determining whether the cancer cell expresses the human MyD88 or does not express the human MyD88 is carried out by detecting the presence or absence of the human MyD88 in the human cancer cell, detecting the quantity of the human MyD88 in the human cancer cell, or detecting nucleic acid that encodes the human MyD88 in the human cancer cell.

11. The method of claim 9, wherein the human MyD88 is detected by Western blot analysis.

12. The method of claim 1, wherein the human Myeloid Differentiation Protein 88 comprises the amino acid sequence of SEQ ID NO:4.

13. The method of claim 5, wherein the human Myeloid Differentiation Protein 88 comprises the amino acid sequence of SEQ ID NO:4.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
tggatacgtt tccttataag                                              20

<210> SEQ ID NO 2
<211> LENGTH: 19
<212> TYPE: DNA
<213> ORGANISM: Artificial Sequence
<220> FEATURE:
<223> OTHER INFORMATION: Synthetic primer

<400> SEQUENCE: 2
gaaatggagg caccccttc                                               19

<210> SEQ ID NO 3
<211> LENGTH: 888
<212> TYPE: DNA
<213> ORGANISM: Homo sapiens

<400> SEQUENCE: 3
atggctgcag gaggtcccgg cgcggggtct gcggccccgg tctcctccac atcctccctt    60
cccctggctg ctctcaacat gcgagtgcgg cgccgcctgt ctctgttctt gaacgtgcgg   120
acacaggtgg cggccgactg gaccgcgctg gcggaggaga tggactttga gtacttggag   180
atccggcaac tggagacaca agcggacccc actggcaggc tgctggacgc ctggcaggga   240
cgccctggcg cctctgtagg ccgactgctc gagctgctta ccaagctggg ccgcgacgac   300
gtgctgctgg agctgggacc cagcattgag gaggattgcc aaaagtatat cttgaagcag   360
cagcaggagg aggctgagaa gcctttacag gtggccgctg tagacagcag tgtcccacgg   420
acagcagagc tggcgggcat caccacactt gatgaccccc tggggcatat gcctgagcgt   480
ttcgatgcct tcatctgcta ttgccccagc gacatccagt ttgtgcagga gatgatccgg   540
caactggaac agacaaacta tcgactgaag ttgtgtgtgt ctgaccgcga tgtcctgcct   600
ggcacctgtg tctggtctat tgctagtgag ctcatcgaaa agaggtgccg ccggatggtg   660
gtggttgtct ctgatgatta cctgcagagc aaggaatgtg acttccagac caaatttgca   720
ctcagcctct ctccaggtgc ccatcagaag cgactgatcc ccatcaagta caggcaatg   780
aagaaagagt tccccagcat cctgaggttc atcactgtct gcgactacac caacccctgc   840
accaaatctt ggttctggac tcgccttgcc aaggccttgt ccctgccc                888

<210> SEQ ID NO 4
<211> LENGTH: 296
<212> TYPE: PRT
<213> ORGANISM: Homo sapiens

<400> SEQUENCE: 4

Met Ala Ala Gly Gly Pro Gly Ala Gly Ser Ala Ala Pro Val Ser Ser
 1               5                  10                  15

Thr Ser Ser Leu Pro Leu Ala Ala Leu Asn Met Arg Val Arg Arg Arg
            20                  25                  30

-continued

```
Leu Ser Leu Phe Leu Asn Val Arg Thr Gln Val Ala Ala Asp Trp Thr
        35                  40                  45
Ala Leu Ala Glu Glu Met Asp Phe Glu Tyr Leu Glu Ile Arg Gln Leu
        50                  55                  60
Glu Thr Gln Ala Asp Pro Thr Gly Arg Leu Leu Asp Ala Trp Gln Gly
65                      70                  75                  80
Arg Pro Gly Ala Ser Val Gly Arg Leu Leu Glu Leu Leu Thr Lys Leu
                85                  90                  95
Gly Arg Asp Asp Val Leu Leu Glu Leu Gly Pro Ser Ile Glu Glu Asp
                100                 105                 110
Cys Gln Lys Tyr Ile Leu Lys Gln Gln Gln Glu Glu Ala Glu Lys Pro
            115                 120                 125
Leu Gln Val Ala Ala Val Asp Ser Ser Val Pro Arg Thr Ala Glu Leu
    130                 135                 140
Ala Gly Ile Thr Thr Leu Asp Asp Pro Leu Gly His Met Pro Glu Arg
145                 150                 155                 160
Phe Asp Ala Phe Ile Cys Tyr Cys Pro Ser Asp Ile Gln Phe Val Gln
                165                 170                 175
Glu Met Ile Arg Gln Leu Glu Gln Thr Asn Tyr Arg Leu Lys Leu Cys
            180                 185                 190
Val Ser Asp Arg Asp Val Leu Pro Gly Thr Cys Val Trp Ser Ile Ala
        195                 200                 205
Ser Glu Leu Ile Glu Lys Arg Cys Arg Arg Met Val Val Val Val Ser
    210                 215                 220
Asp Asp Tyr Leu Gln Ser Lys Glu Cys Asp Phe Gln Thr Lys Phe Ala
225                 230                 235                 240
Leu Ser Leu Ser Pro Gly Ala His Gln Lys Arg Leu Ile Pro Ile Lys
                245                 250                 255
Tyr Lys Ala Met Lys Lys Glu Phe Pro Ser Ile Leu Arg Phe Ile Thr
            260                 265                 270
Val Cys Asp Tyr Thr Asn Pro Cys Thr Lys Ser Trp Phe Trp Thr Arg
        275                 280                 285
Leu Ala Lys Ala Leu Ser Leu Pro
    290                 295
```